United States Patent
Kahana et al.

(10) Patent No.: US 10,449,359 B2
(45) Date of Patent: Oct. 22, 2019

(54) METHOD AND APPARATUS FOR IMPROVING COGNITIVE PERFORMANCE

(71) Applicant: The Trustees of the University of Pennsylvania, Philadelphia, PA (US)

(72) Inventors: Michael Kahana, Merion Station, PA (US); Daniel S. Rizzuto, Philadelphia, PA (US)

(73) Assignee: THE TRUSTEES OF THE UNIVERSITY OF PENNSYLVANIA, Philadelphia, PA (US)

( * ) Notice: Subject to any disclaimer, the term of this patent is extended or adjusted under 35 U.S.C. 154(b) by 54 days.

(21) Appl. No.: 15/545,927

(22) PCT Filed: Jan. 22, 2016

(86) PCT No.: PCT/US2016/014438
§ 371 (c)(1),
(2) Date: Jul. 24, 2017

(87) PCT Pub. No.: WO2016/118811
PCT Pub. Date: Jul. 28, 2016

(65) Prior Publication Data
US 2018/0021579 A1    Jan. 25, 2018

Related U.S. Application Data

(60) Provisional application No. 62/107,358, filed on Jan. 24, 2015, provisional application No. 62/238,871, filed on Oct. 8, 2015.

(51) Int. Cl.
*A61N 1/36* (2006.01)
*A61B 5/0484* (2006.01)
(Continued)

(52) U.S. Cl.
CPC ........ *A61N 1/36082* (2013.01); *A61B 5/0484* (2013.01); *A61N 1/0531* (2013.01);
(Continued)

(58) Field of Classification Search
CPC .............. A61N 1/36082; A61N 1/0531; A61N 1/36064; A61N 1/36067; A61N 1/36135;
(Continued)

(56) References Cited

U.S. PATENT DOCUMENTS 6,309,361 B1 * 10/2001 Thornton ............. A61B 5/0484
600/544
2002/0188217 A1   12/2002 Farwell
(Continued)

OTHER PUBLICATIONS

Supplementary European Search Report, Patent Application No. 16740807.9-1124/3247267 PCT/US2016014438, dated Jun. 26, 2018, 8 pages.
(Continued)

*Primary Examiner* — Carl H Layno
*Assistant Examiner* — Erin M Piateski
(74) *Attorney, Agent, or Firm* — Morgan, Lewis & Bockius LLP

(57) ABSTRACT

A method for delivering electrical stimulation to alter a cognitive state of a user, the method comprising: monitoring a brain signal from the user via one or more intracranial electrodes implanted in the brain of the user while the user is presented with a stimulus; comparing the brain signal to a testing phase biomarker, wherein the testing phase biomarker is derived from a cognitive test performed on a contributor during a testing phase; delivering electrical stimulation to a brain of the user based on the comparing step to steer the brain of the user towards a high performance cognitive state.

29 Claims, 15 Drawing Sheets

(51) Int. Cl.
*G06F 19/00* (2018.01)
*A61N 1/05* (2006.01)

(52) U.S. Cl.
CPC ..... *A61N 1/36064* (2013.01); *A61N 1/36067* (2013.01); *A61N 1/36135* (2013.01); *G06F 19/3481* (2013.01); *A61N 1/0534* (2013.01)

(58) Field of Classification Search
CPC .. A61N 1/0534; A61B 5/0484; G06F 19/3481
USPC .......................................................... 607/45
See application file for complete search history.

(56) References Cited

U.S. PATENT DOCUMENTS

| | | | |
|---|---|---|---|
| 2008/0004660 A1 | 1/2008 | Assaf et al. | |
| 2008/0027346 A1 | 1/2008 | Litt et al. | |
| 2010/0292545 A1 | 11/2010 | Berka et al. | |
| 2011/0112427 A1* | 5/2011 | Phillips | A61B 5/048 600/544 |
| 2012/0066238 A1 | 3/2012 | Fadem et al. | |
| 2012/0116475 A1 | 5/2012 | Nelson et al. | |
| 2012/0150545 A1 | 6/2012 | Simon | |
| 2012/0221075 A1 | 8/2012 | Bentwich | |
| 2014/0057232 A1* | 2/2014 | Wetmore | G09B 19/00 434/236 |
| 2014/0081347 A1* | 3/2014 | Nelson | A61N 1/36082 607/45 |
| 2014/0107521 A1 | 4/2014 | Galan | |
| 2014/0171757 A1 | 6/2014 | Kawato et al. | |
| 2014/0316230 A1 | 10/2014 | Denison et al. | |
| 2014/0323899 A1 | 10/2014 | Silberstein | |

OTHER PUBLICATIONS

International Patent Application No. PCT/US2016/014438, Notification of Transmittal of the International Search Report, and the Written Opinion of the International Searching Authority, or the Declaration dated Jul. 29, 2016, 11 pages.

* cited by examiner

FIG. 10A
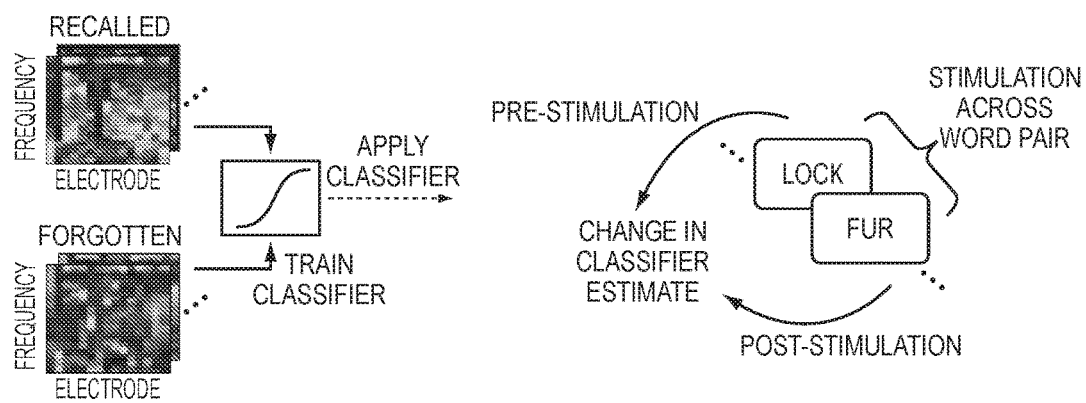
FIG. 10B
FIG. 10C

METHOD AND APPARATUS FOR IMPROVING COGNITIVE PERFORMANCE

CROSS-REFERENCE TO RELATED APPLICATIONS

The present application is a U.S. National Stage Entry of International Patent Application No. PCT/US2016/014438, entitled "Method and Apparatus for Improving Cognitive Performance," filed on Jan. 22, 2016, which in turn claims the benefit of U.S. Provisional Patent Application No. 62/107,358, entitled "Method and Apparatus for Improving Cognitive Performance," filed on Jan. 24, 2015 and U.S. Provisional Patent Application No. 62/238,871, entitled "Method and Apparatus for Improving Cognitive Performance," filed on Oct. 8, 2015, all of which are incorporated by reference herein in their entireties.

GOVERNMENT SUPPORT

The present invention was made with Government support under Grant No. N66001-14-2-4032 awarded by Space and Naval Warfare Systems Center, Pacific. The Government has certain rights in the invention.

BACKGROUND

The present invention generally relates to a method and apparatus for improving cognitive performance through the application of brain stimulation.

SUMMARY

In one embodiment there is a method for creating a biomarker indicative of high-performance or low-performance cognition, the method comprising: presenting a stimulus to a contributor; receiving a response and a brain signal from the contributor; associating the response and the brain signal with the stimulus; determining that the brain signal corresponds to one of: a high-performance cognitive state of the contributor and a low-performance cognitive state of the contributor; and generating a biomarker using the brain signal that corresponds to the one of: the high-performance cognitive state of the contributor and low-performance cognitive state of the contributor.

In a further embodiment, the biomarker is a set of features (such as the time-frequency decomposition of the voltage traces recorded across an array of electrodes) that distinguish a brain signal corresponding to a high-performance cognitive state from a brain signal corresponding to a low-performance cognitive state.

In a further embodiment, the method further comprising: transforming a biomarker with a large set of features into a biomarker comprising one or several numbers, which distinguishes a brain signal corresponding to a high-performance cognitive state from a brain signal corresponding to a low-performance cognitive state.

In a further embodiment, the biomarker is a threshold corresponding to a feature of the brain signal.

In a further embodiment, the method further comprising: transmitting the biomarker to a modulation device.

In a further embodiment, the method further comprising: receiving the brain signal from a modulation device connected to a brain of the contributor.

In a further embodiment, the method further comprising: associating the response with the stimulus by comparing the response to the stimulus.

In a further embodiment, the method further comprising: associating the brain signal with the stimulus by determining whether a time period where the brain signal is monitored by a modulation device overlaps with a time period where the stimulus is presented to the contributor.

In a further embodiment, if the response matches the stimulus, the response is a positive response.

In a further embodiment, the brain signal corresponds to the high performance cognitive state of the contributor if the brain signal is associated with a stimulus having a positive response or a fast reaction time.

In a further embodiment, if the response does not match the stimulus, the response is a negative response.

In a further embodiment, the brain signal corresponds to the low performance cognitive state of the contributor if the brain signals are associated with a stimulus having a negative response or a slow reaction time.

In a further embodiment, the high performance cognitive state is an accurate memory.

In a further embodiment, the low performance cognitive state is an inaccurate memory.

In a further embodiment, the method further comprising: storing the biomarker in a database.

In a further embodiment, the brain signal is one or more brain signals from one or more contributors.

In one embodiment, there is a system for creating a biomarker indicative of high performance or low performance cognitive state according to any of the methods in the preceding claims.

In one embodiment, there is a non-transitory computer readable storage medium having stored thereon computer-executable instructions which, when executed by a processor, perform any of the methods for creating a biomarker indicative of high performance or low performance cognitive state in the preceding claims.

In one embodiment, there is a method for delivering stimulation to alter a cognitive state of a user, the method comprising: monitoring a brain signal from the user (optionally while the user is presented with a stimulus); comparing the brain signal to a testing phase biomarker, wherein the testing phase biomarker is derived from a cognitive test performed on a contributor during a testing phase; delivering stimulation to a brain of the user based on the comparing step to steer the brain of the user towards high performance cognitive state.

In one embodiment, there is a method to optimize the location and parameters of stimulation to alter the cognitive state of the user, the method comprising: monitoring a brain signal from the user; stimulating the user's brain at varied locations using varied stimulation parameters; comparing the user's brain response with the testing phase biomarker to identify the optimal stimulation location and parameters.

In a further embodiment, the testing phase biomarker is indicative of a low performance cognitive state of the user as determined based on a cognitive test performed on the contributor.

In a further embodiment, the testing phase biomarker is indicative of a high performance cognitive state of the user as determined based on a cognitive test performed on the contributor.

In a further embodiment, the contributor is the user.

In a further embodiment, the contributor is a plurality of contributors.

In a further embodiment, the contributor is different than the user.

In a further embodiment, the method further comprising: updating the testing phase biomarker based on the brain signal of the user and a response of the user to the stimulus.

In a further embodiment, electrical stimulation is delivered to a single subfield of a hippocampus.

In a further embodiment, electrical stimulation is delivered to multiple regions of the brain of the user.

In one embodiment, there is a system for delivering electrical stimulation to alter a cognitive state of a user according to any of the methods in the preceding claims.

In one embodiment, there is a non-transitory computer readable storage medium having stored thereon computer-executable instructions which, when executed by a processor, perform any of the methods for delivering electrical stimulation to alter a cognitive state of a user in the preceding claims.

BRIEF DESCRIPTION OF THE SEVERAL VIEWS OF THE DRAWINGS

The following detailed description of embodiments of the invention will be better understood when read in conjunction with the appended drawings of an exemplary embodiment. It should be understood, however, that the invention is not limited to the precise arrangements and instrumentalities shown.

In the drawings.

Figure 5:
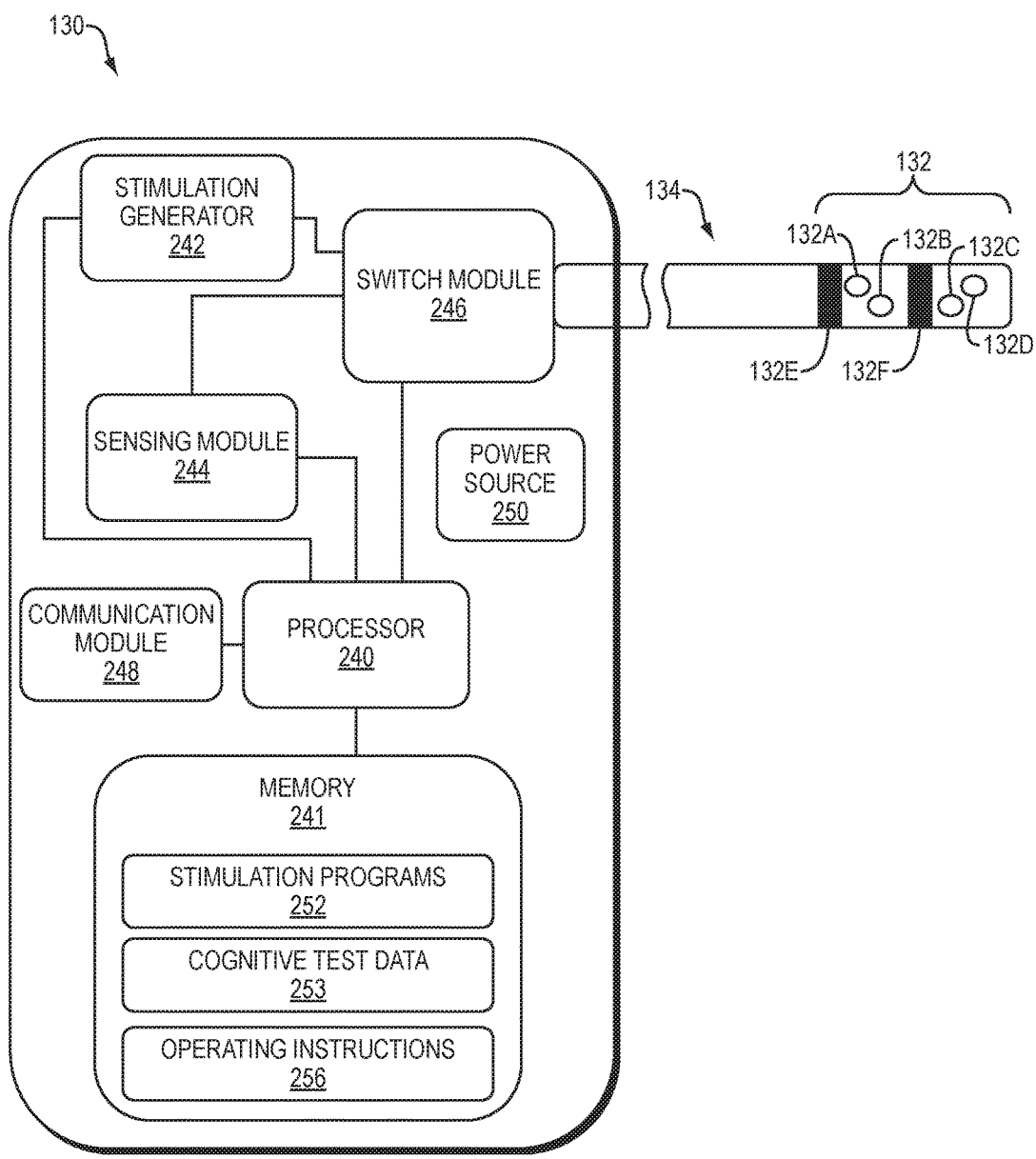
Figure 6:
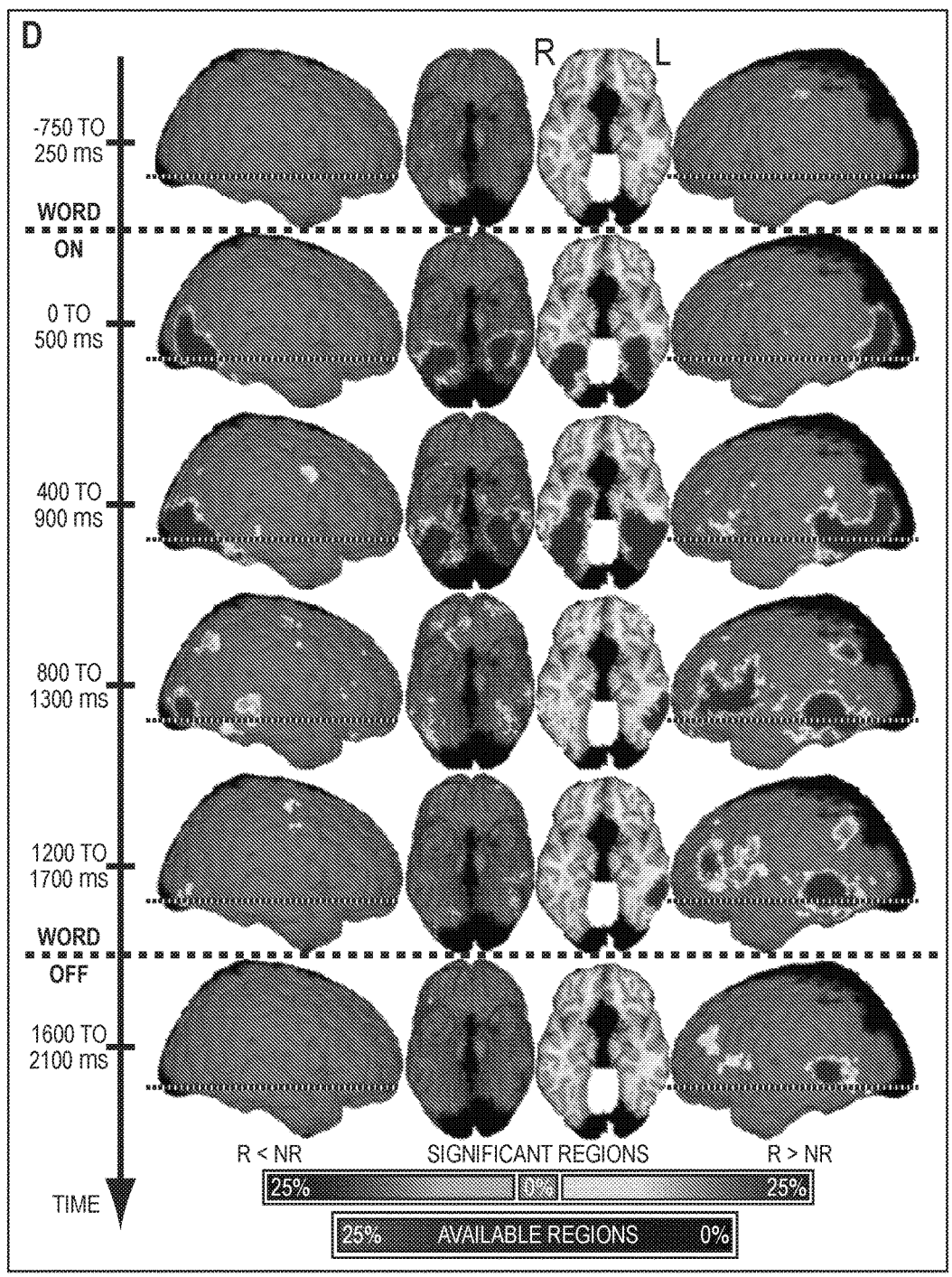
Figure 7:
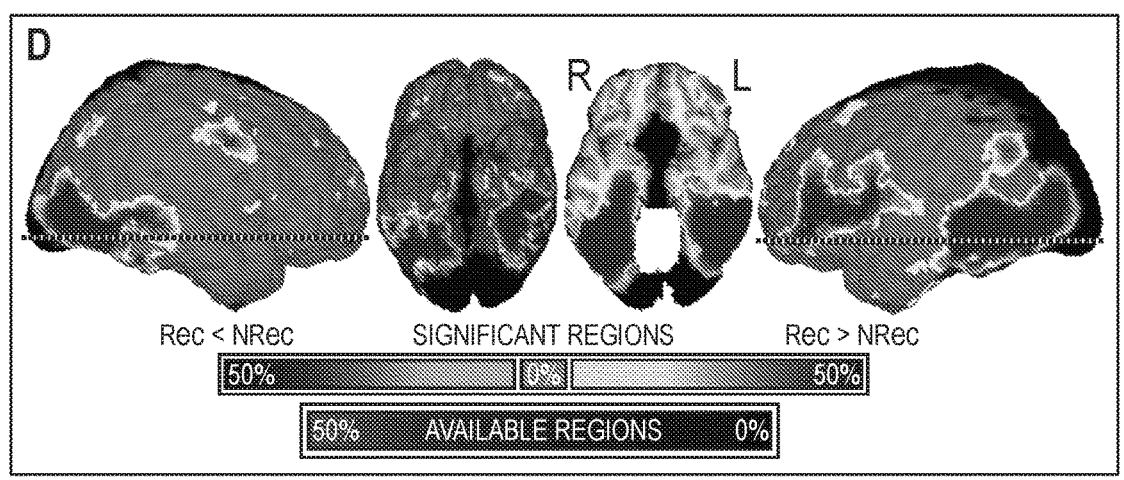
Figure 8:
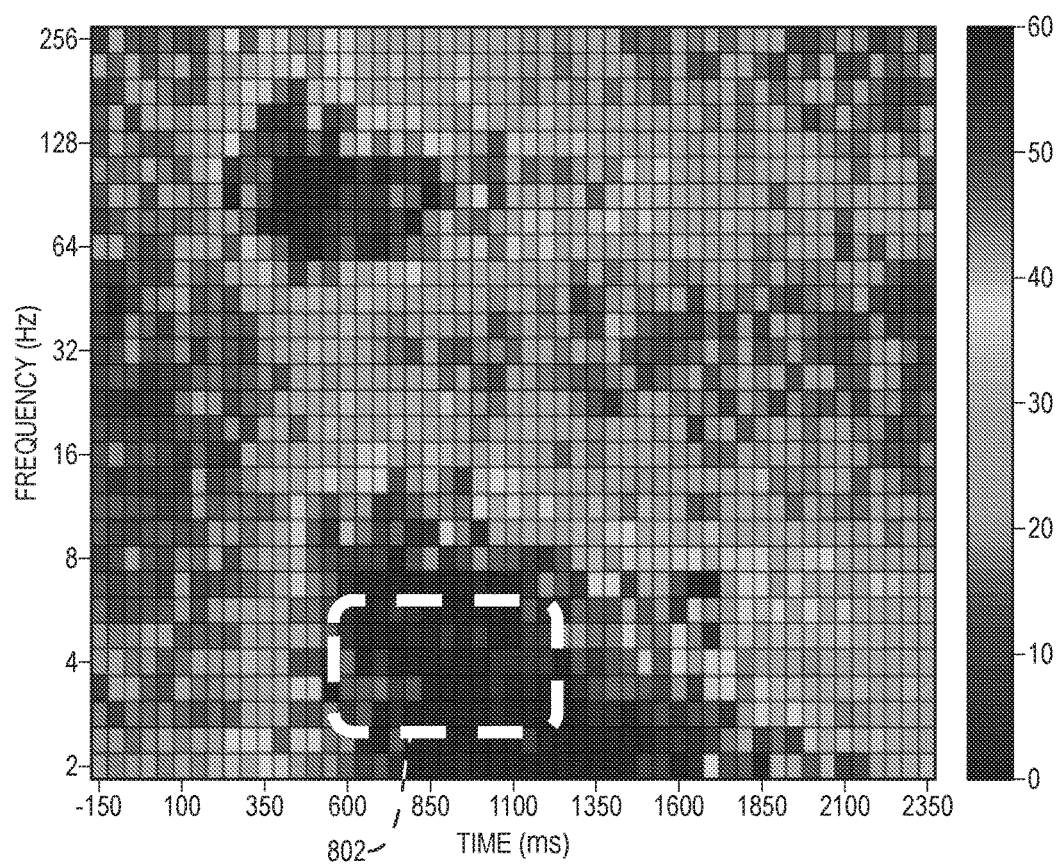
Figure 9:
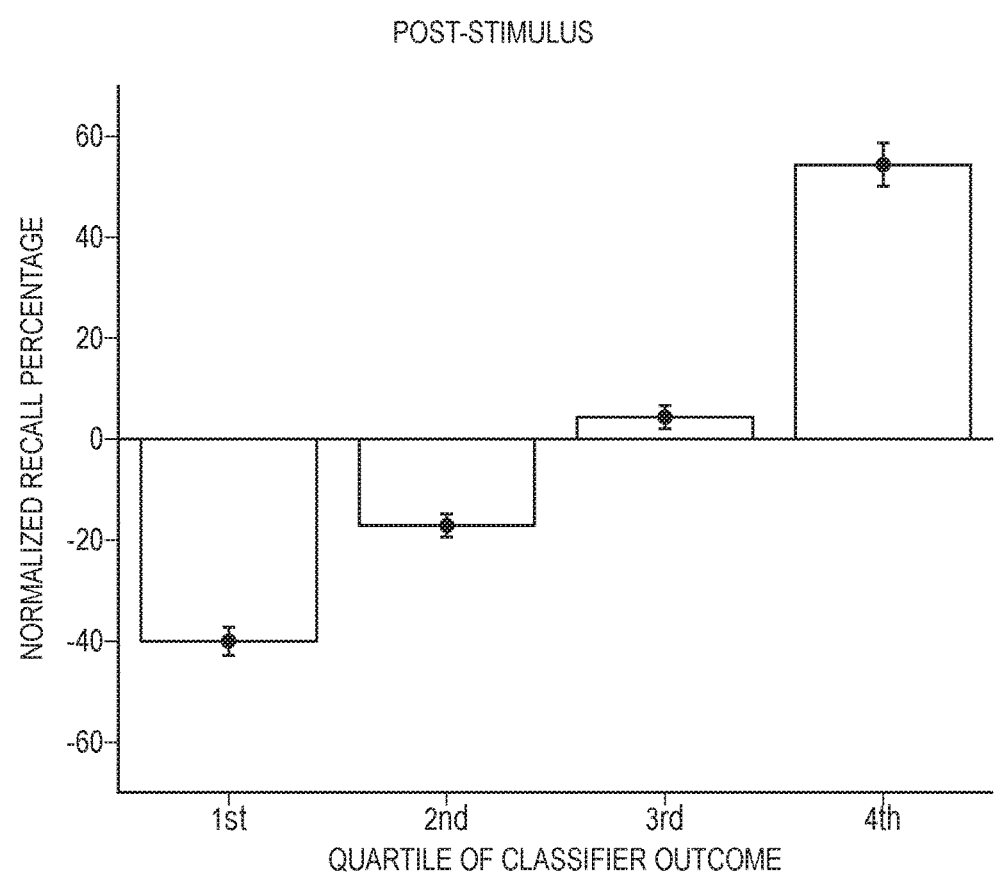

memory cognition) according to at least one embodiment of the invention;

FIG. 5 is a functional block diagram illustrating components of modulation device according to at least one embodiment of the invention;

FIG. 6 illustrates an example of neural activity in a brain while a user is attempting to accurately create a memory over time according to at least one embodiment of the invention;

FIG. 7 illustrates an example of neural activity in a brain while a user is attempting to accurately create a memory according to at least one embodiment of the invention;

FIG. 8 illustrates an exemplary map of potential performance improvement that can be gained from biomarkers at various time points and frequencies according to at least one embodiment of the invention; and FIG. 9 illustrates potential performance gains available by reinstating the biomarkers associated with various quartiles of performance according to at least one embodiment of the invention.

FIG. 10A illustrates a delayed free recall task performed by subjects while local field potentials (LFPs) from surface and depth electrodes implanted subdurally according to at least one embodiment of the invention.

FIG. 10B illustrates a time-frequency spectral decomposition performed on the recordings from each electrode during all word presentation periods according to at least one embodiment of the invention. In this embodiment, mean power across the encoding period within each frequency band was used as input to a logistic regression classifier trained to discriminate whole-brain spectral patterns predictive of later recall from later forgetting.

FIG. 10C illustrates the delayed free recall task performed by the subjects during a later session, while targeted electrical stimulation was delivered to an adjacent pair of electrode contacts according to at least one embodiment of the invention. In this embodiment, the trained logistic regression model was applied to the whole-brain LFP data recorded just prior to delivery of stimulation, and the model's estimates of encoding efficiency at the time of stimulation delivery was used to assess the effects of stimulation on memory performance.

FIGS. 11A-J illustrate graphs showing logistic regression classifier performance data for two example subjects and the group according to at least one embodiment of the invention.

Figure 11A:
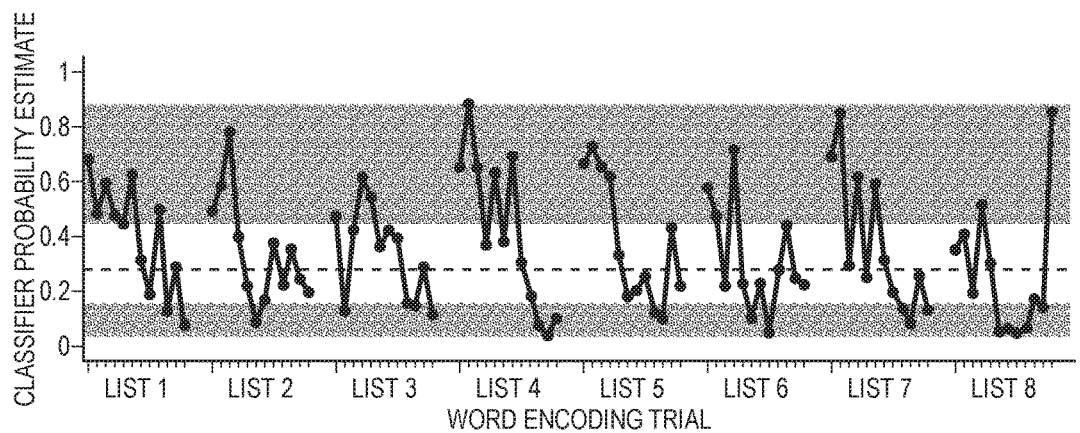
Figure 11B:
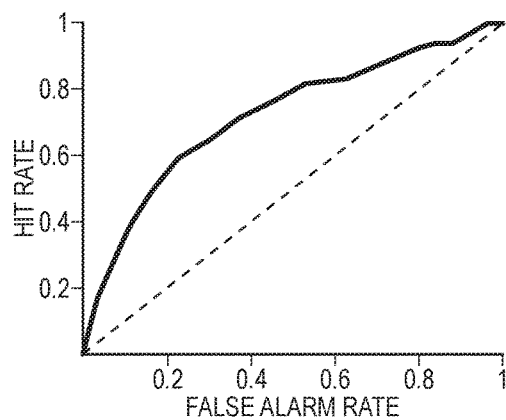
Figure 11C:
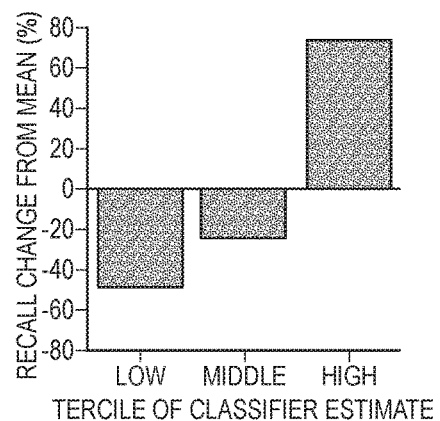
Figure 11D:
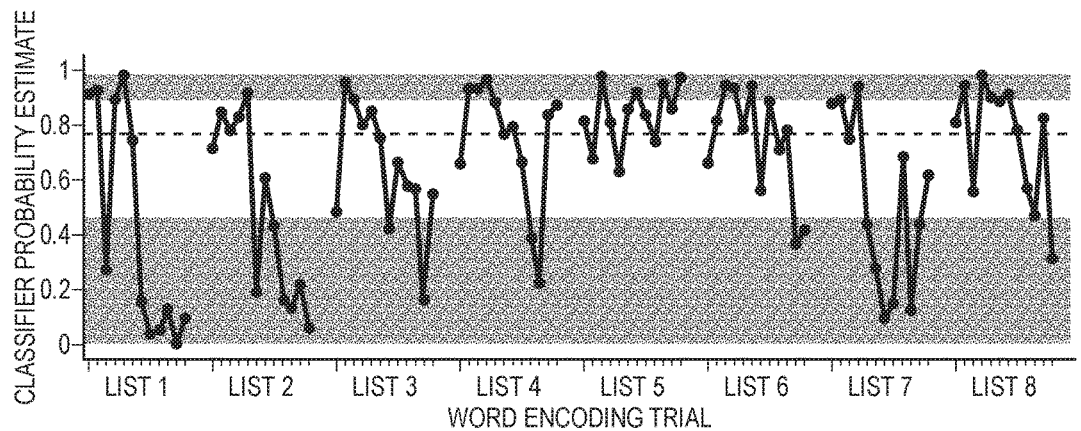

FIGS. 11A and 11D illustrate graphs showing classifier output probability for an eight-list period of the delayed free recall task according to at least one embodiment of the invention. In this embodiment, gray shaded regions correspond to the top and bottom terciles of the distribution of classifier probability estimates; median indicated by the dashed line. In this embodiment, red shaded portions correspond to later recalled words; and blue shaded portions correspond to later forgotten words.

Figure 11E:
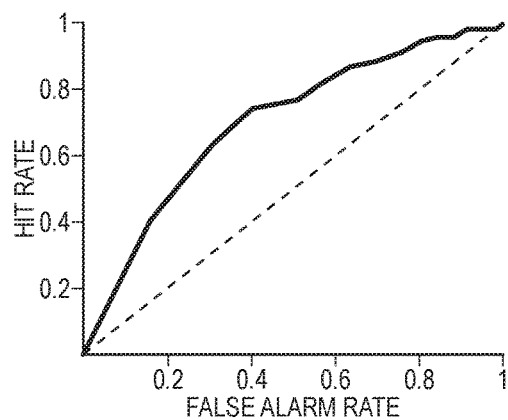

FIGS. 11B and 11E illustrate graphs showing area under the curve (AUC) for both subjects was significantly greater than chance (estimated using a permutation procedure in which words were randomly assigned to recalled/not-recalled category), in accordance with at least one embodiment of the invention.

Figure 11F:
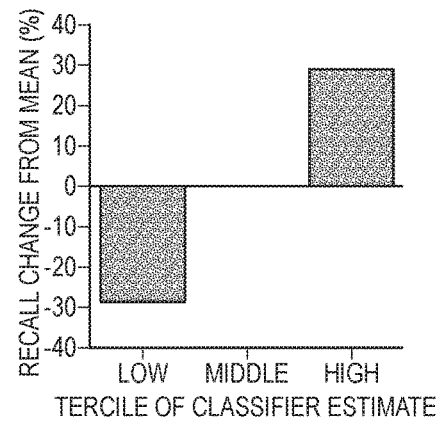

FIGS. 11C and 11F illustrate graphs showing example subject recall performance represented as percentage deviation from the (subject) mean, separated by tercile of the classifier's encoding efficiency estimate for each encoded word, according to at least one embodiment of the invention.

Figure 11G:
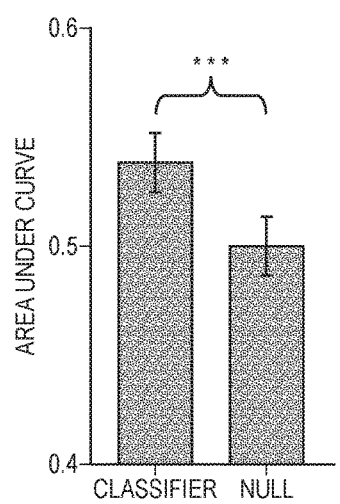

FIG. 11G illustrates a graph showing average AUC was significantly greater than chance across the group ($P<0.0001$), according to at least one embodiment of the invention.

Figure 11H:
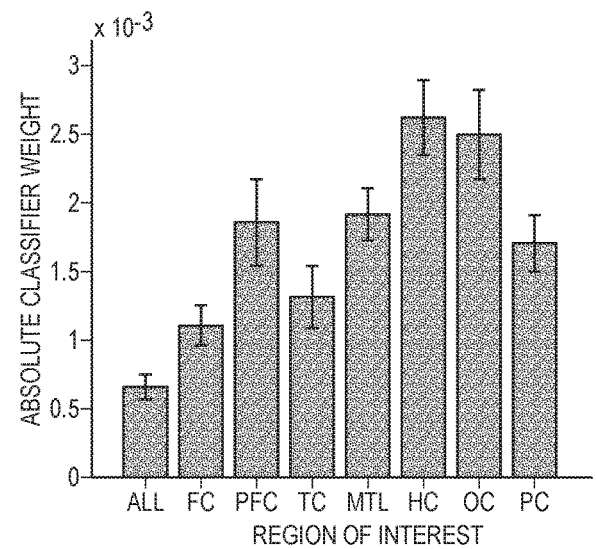

FIG. 11H illustrates a graph showing average absolute classifier weights across patients for broad regions of interest, according to at least one embodiment of the invention, where All=all electrodes; FC=frontal cortex; PFC=prefrontal cortex; TC=temporal cortex; MTL=medial temporal lobe (including hippocampus, amygdala and cortex); HC=hippcampus; OC=occipital cortex; PC=parietal cortex.

Figure 11I:
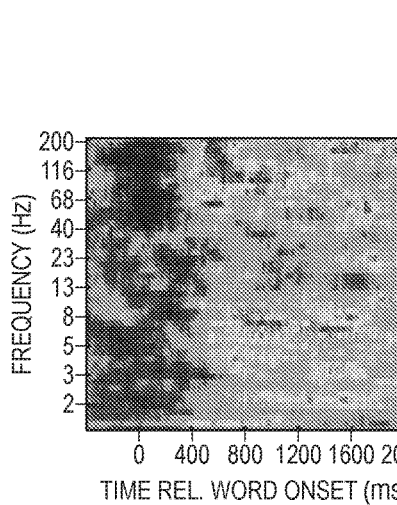

FIG. 11I illustrates a graph showing change in recall performance from the top to bottom tercile of classifier estimates, as a function of time and frequency, according to at least one embodiment of the invention.

Figure 11J:
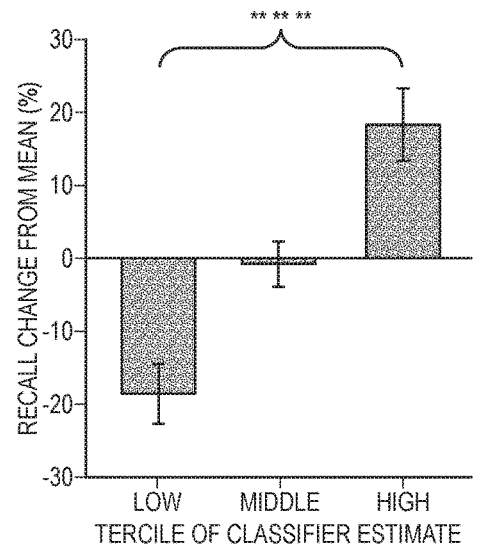

FIG. 11J illustrates a group mean tercile plot showing significantly decreased performance for words that the classifier assigned to the lowest encoding efficiency bin compared to words assigned to the highest bin ($P<0.0002$), according to at least one embodiment of the invention.

Figure 12A:
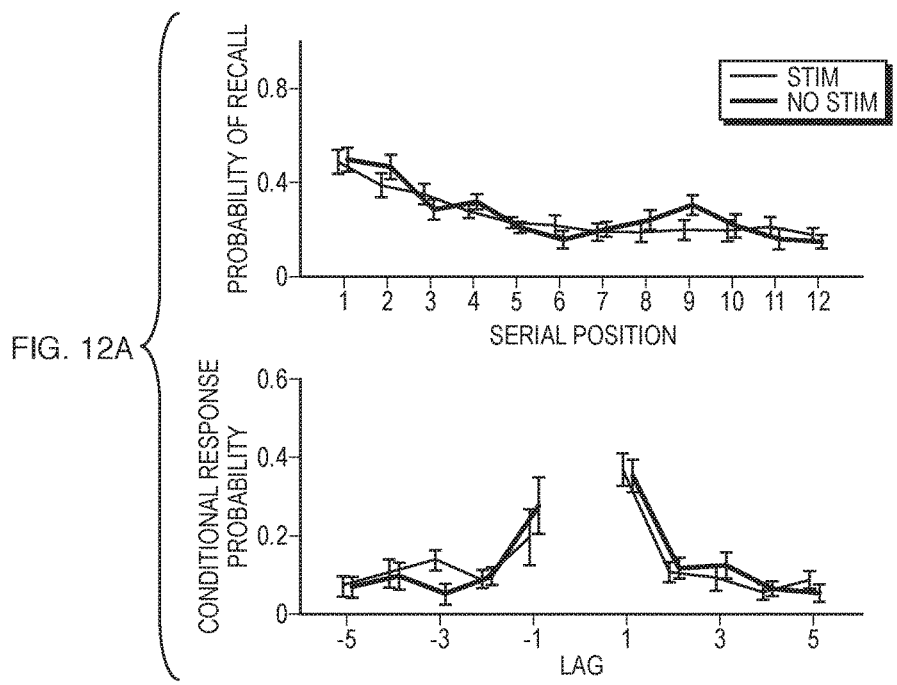

FIG. 12A illustrates a graph showing recall probability as a function of serial position (top) and inter-item lag (bottom) do not significantly differ as a function of stimulation condition, according to at least one embodiment of the invention.

Figure 12B:
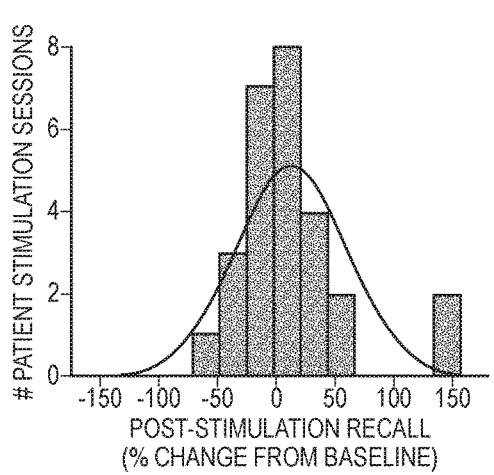

FIG. 12B illustrates a graph showing stimulation's effect on memory performance varied across subjects (mean change in normalized percent recall=8.9 9.3%, p>0.33), according to at least one embodiment of the invention.

Figure 12C:
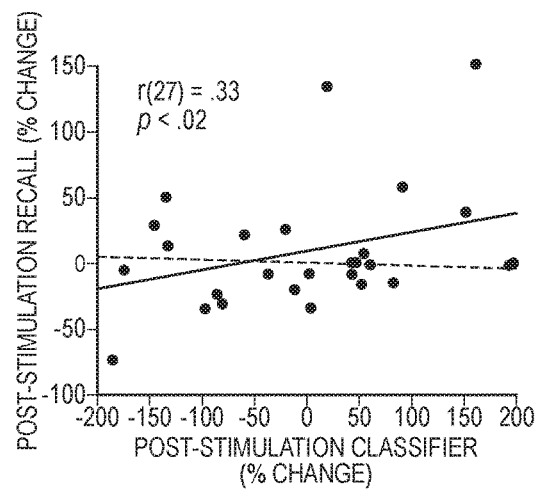

FIG. 12C illustrates a graph showing the behavioral effect of stimulation correlated with the change in encoding efficiency estimated by the classifier (r(25)=0.33, p<0.02, permutation test), according to at least one embodiment of the invention. Dashed line indicates mean permutation-derived regression line.

Figure 13:
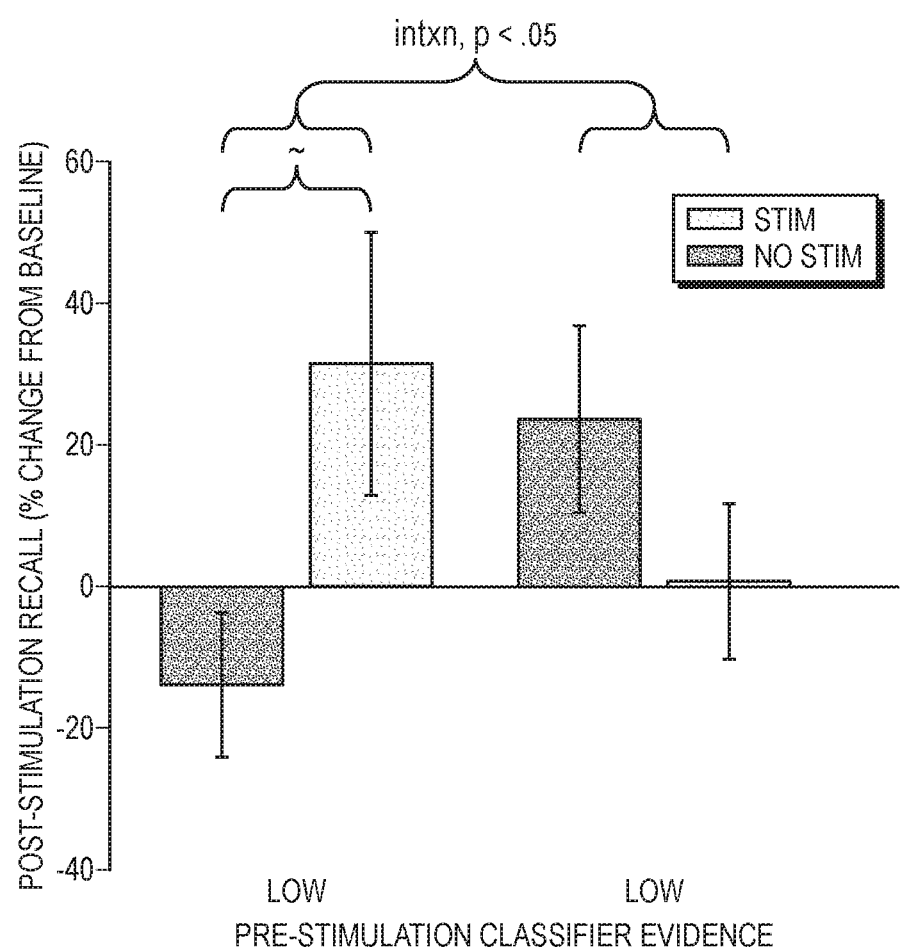

FIG. 13 illustrates a graph showing the effects of stimulation depend on the encoding state at the time of delivery, according to at least one embodiment of the invention. Stimulation's effect on memory is a function of the encoding efficiency at the time stimulation is applied, according to at least one embodiment of the invention. When encoding efficiency was low, stimulation tended to increase memory relative to matched intervals in the NoStim condition (p=0.06), according to at least one embodiment of the invention.

DETAILED DESCRIPTION

I. Overview

The human brain is composed of billions of neurons electrically interconnected and organized into various areas to perform a variety of functions. The electrical activation and/or deactivation of neurons or groups of neurons is largely responsible for the function of the brain and communication amongst the various areas of the brain along the networks.

In some instances, brain stimulation can be therapeutically applied in order to prevent the onset of or treat an undesirable state, such as in the cases of epilepsy or tremors associated with Parkinson's Disease. In neurological disease, there is typically a clear separation between 'normal' and 'abnormal' brain function. This is the case, for example, in epilepsy where abnormal function is marked not only by seizures, but also by neurophysiological markers of epileptic network activity (e.g., spikes and sharp waves) that are present even when the brain is not seizing.

In the absence of neurological disease, brain functions can be highly variable across time. In fact, it is common for the brain to fluctuate between states along a spectrum of low-performance cognitive state(s) to high-performance cognitive state(s) for a given user while a cognitive task is being performed or when different cognitive tasks are performed over time, yet all of these cognitive states from high-performance cognitive states to low-performance cognitive states may be classified as "normal" brain function. This fluctuation between a high-performance cognitive state and a low-performance cognitive state may occur on a moment-by-moment, trial-by-trial and even day-by-day basis. For example, a user might be asked to remember a list of twelve words, but only be able to recall six words at a later date. One of the reasons for incomplete recall may be the user fluctuating between a high-performance cognitive state and a low-performance cognitive state while trying to remember each word or patterns of words at the time of memorization, at the time of recall or both.

Figure 1:
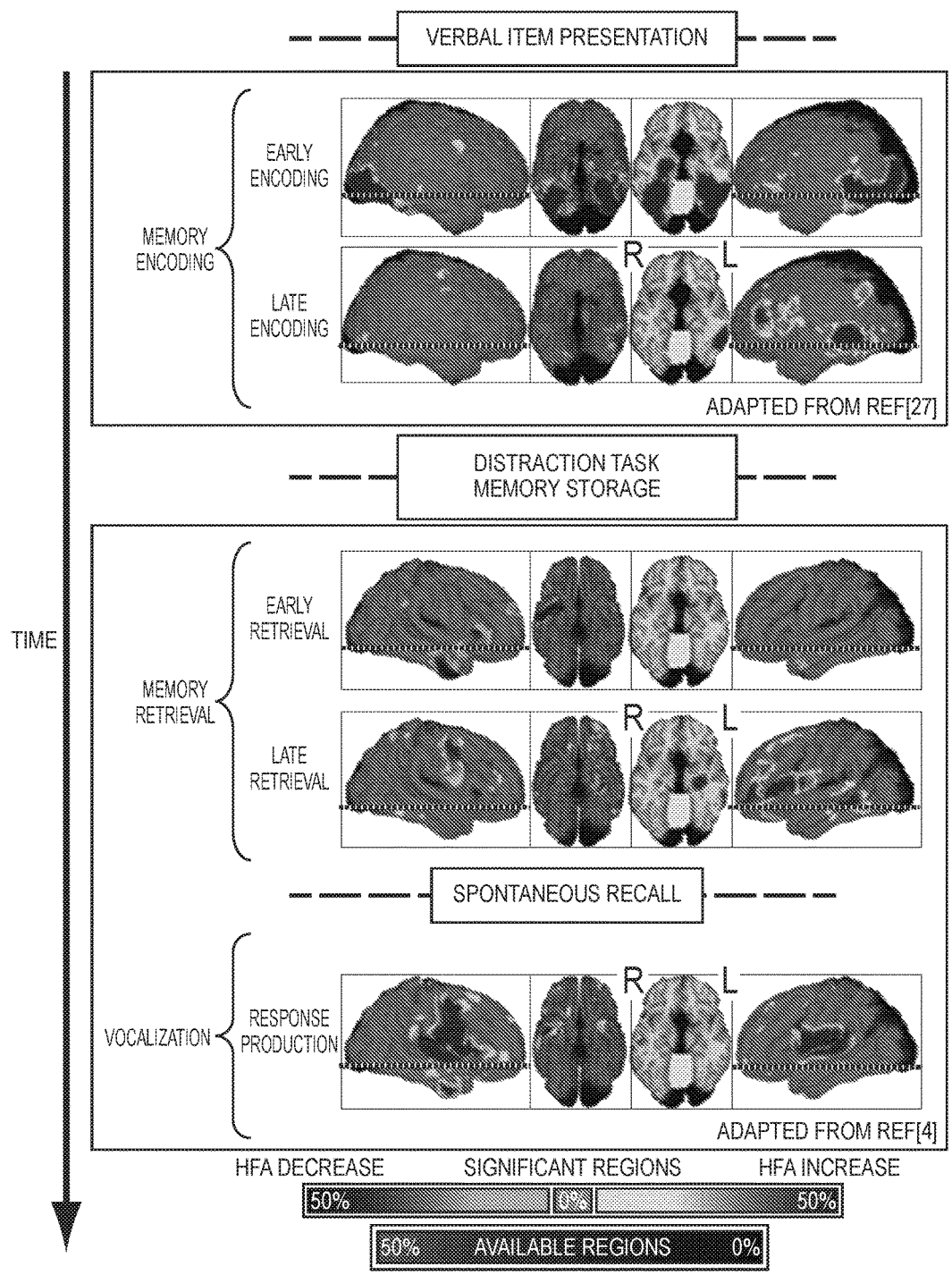
FIG. 1 illustrates examples of how different brain regions are activated to perform a brain function according to at least one embodiment of the invention.

It is generally thought that the activation of numerous neurons, among other types of network function, may be necessary to carry out each brain function when performing a cognitive task (e.g., creating a memory, solving a puzzle, recall of earlier memorized information, etc.). FIG. 1 illustrates examples of how different brain regions are activated to perform a brain function according to at least one embodiment of the invention. This example illustrates the primary stages of a memory task: memory encoding, memory retrieval and vocalization. As shown, different brain regions are activated during different stages, and even sub-stages such as early encoding and late encoding. Activation for memory encoding, retrieval and vocalization is represented through shading of the brain areas, where regions exhibiting statistically significant increased or decreased activation are shaded in dark gray. The brain signals associated with each stage can be used as biomarkers indicative of accurate or inaccurate memory formation, as explained below in more detail.

Therefore, to alter cognition in embodiments of the invention, neural activity and/or engagement may be tracked while a user is performing a cognitive task and stimulation may be delivered to a user to activate or deactivate populations of neurons associated with the desired state of performance (e.g., high performance or low-performance cognitive states) for a given cognitive task. For example, a method or device may detect a low-performance cognitive state associated with increased likelihood of memory loss and stimulate portions of the brain at appropriately selected targets to transition the brain to an enhanced or high performance cognitive state to diminish the likelihood of memory loss. Alternatively, a method or device may detect a high-performance cognitive state associated with increased likelihood of memory creation and stimulate in the brain at appropriately selected targets to prolong the length of time that the brain is in the high-performance cognitive state to thereby increase the potential of the user to correctly perform the cognitive task, among other things.

The fluctuation or variability between high-performance cognitive states and low-performance cognitive states exists in all people, such as those with normal brain function as well as those with brain impairments (e.g., Alzheimer's disease). In other words, even for a user with normal brain function, that user may fluctuate between high-performance cognitive states and low-performance cognitive states for a given task or tasks. Therefore, in order to improve cognitive performance, it is not enough to simply stimulate the brain to reduce symptoms of brain impairments. Instead, it is necessary to determine whether a user is in a high-performance cognitive state or a low-performance cognitive state for a given task or tasks by comparing brain activity (e.g., the electrical signals that may be recorded from electrodes as well as other biomarkers of brain function such as the concentration of neurotransmitters) of a user to one or more biomarkers indicative of a high-performance cognitive state or a low-performance cognitive state regardless of whether or not the user has brain impairment. By identifying the target for an intervention (i.e., modulate the brain when it is in a certain cognitive state) and monitoring the variability in the brain state, one can guide the user's brain to a desired cognitive state using brain stimulation. In addition, it is also possible to guide the user's brain to an enhanced-performance cognitive state, in which the user performs beyond his or her normal limits.

In one embodiment, the use of a system or device of the present invention includes a multi-phase process to ultimately alter cognition of a user.

In the first phase, known as the testing phase, a cognitive test is presented and cognitive tasks (e.g., memory exercises/games) are performed by one or more biomarker contributors. Biomarkers of the measured brain signals are assessed during the cognitive tasks by correlating these brain signals with task performance, and identifying a set of one or more biomarkers that predict task performance (e.g. amplitude, band power, phase, etc.). These biomarkers may be saved in a memory or entered into a database. The biomarkers may also be associated with a level of cognitive performance of the given contributor (e.g., enhanced-performance cognitive state, high-performance cognitive state or low-performance cognitive state) for a given cognitive task based upon the test results. While performance and biomarkers indicative of the performance may be contributor specific, in some embodiments similar biomarkers indicative of performance during a given cognitive task across multiple contributors may also be created. Alternatively, custom biomarker(s) may also be created where the custom biomarker(s) is created without the use of input or testing from a biomarker contributor. Alternatively, modified or hybrid biomarker from one or more contributors can be created.

In some embodiments, if a large set of biomarkers is identified, the set may be reduced to one or more biomarker representative values using one or more dimensionality reduction algorithms (such as linear classifiers, support vector machines, neural networks, etc.) to classify the brain signals into enhanced-performance, high-performance and low-performance cognitive states. In some embodiments, the number of biomarker representative values is less than 25, less than 20, less than 15, less than 10, less than 5, less than 4, less than 3, or 1.

In some embodiments, there is an intermediate phase, known as the stimulation optimization phase, where one or more electrical stimulations may be applied to the biomarker recipient's brain at varied locations and using varied stimulation parameters (such as amplitude, frequency, pulse width, etc.) to determine the effects of each parameter set on the set of biomarkers identified in the testing phase. In some embodiments, stimulation locations and parameter sets may be evaluated by comparing the recipient's brain response to a particular location and parameter set with the set of biomarkers identified in the testing phase.

In the next phase, known as the modulation phase, electrical stimulation is applied to a brain of a biomarker recipient to modulate the recipient's level of cognitive performance. In one embodiment, the initial set of one or more stimulation locations and parameters for electrical stimulation are chosen in the stimulation optimization phase based on the degree to which the stimulation locations and parameters produced a match (e.g., correlation) between the recipient's brain signals during the stimulation optimization phase and a set of one or more biomarkers identified in the testing phase.

In some embodiments, the amount and location of electrical stimulation is based on an earlier developed brain signal biomarker pattern or biomarkers patterns or a contemporaneously developed biomarker that is indicative of a desired level of cognitive performance for a given cognitive task to thereby enforce or alter a desired level of performance of the recipient.

Specifically, electrical stimulation can be applied to a recipient, where the stimulation imparts a pattern of electrical activity in the recipient's brain (e.g., such as increased amplitude of a particular brain wave, or increased synchronicity between brain waves at two or more loci) corresponding to a set of biomarkers having an associated performance level. Therefore, the recipient's brain activity can be modulated to match the desired biomarkers, leading to an improvement in performance during the cognitive task.

The stimulation optimization phase can be repeated as often as needed to optimize the effectiveness of the modulation phase in improving the recipient's cognitive performance.

In one embodiment, the altered cognition resultant from the modulation phase may be improved cognition and/or ability to perform a given cognitive task. In another embodiment, the altered cognition may be impaired cognition. In one embodiment, the biomarker may be indicative of supra-normal (i.e. enhanced) performance for a given cognitive task for a given user. One of ordinary skill in the art would appreciate that the systems and methods described herein could be used for the purposes of improving or impairing cognition.

Referring to the drawings in detail, wherein like reference numerals indicate like elements throughout, there is shown in FIGS. 1-13, systems and methods, generally designated, in accordance with exemplary embodiments of the present invention.

II. Definitions

Biomarker—In one embodiment, a biomarker is a characteristic of one or more brain signals (e.g., activation/deactivation of neurons, electrical potential changes in the brain or chemical changes in the brain) from one or more contributors that indicates the presence of a particular brain state (e.g., enhanced performance cognition, high performance cognition or low performance cognition).

Cognitive task—In one embodiment, a cognitive task is a task that requires at least one mental process and for which a performance metric can be calculated (e.g. accuracy or reaction time).

High performance cognitive state—In one embodiment, a high performance cognitive state is a brain state associated with favorable performance in a cognitive task (e.g. high accuracy or fast reaction time). In one embodiment, the spectrum of low-performance cognitive state(s) to high-performance cognitive state(s) can be a statistical distribution (e.g. a normal distribution characterized by a mean and standard deviation, or a skewed distribution like the gamma or ex-Gaussian which often describes variation in performance with a fixed lower bound). In some embodiments, a high-performance cognitive state may be any cognitive state that is in the top X-th percentile of the range, where X could be any value in the range of 0-100, along the spectrum of low-performance and high-performance cognitive states. In some embodiments, a high-performance cognitive state may be defined in relation to the variability of the distribution, as in the case of a normal distribution where such states could be defined in terms of their standard deviations from the mean (e.g., performance exceeding the mean +X standard deviations, where X could be 3, 2, 1, 0, −1, −2, 3, etc.).

Low performance cognitive state—In one embodiment, a low performance cognitive state is a brain state associated with unfavorable performance in a cognitive task (e.g. low accuracy or slow reaction time). In one embodiment, the spectrum of low-performance cognitive state(s) to high-performance cognitive state(s) can be a statistical distribution (e.g. a normal distribution characterized by a mean and standard deviation, or a skewed distribution like the gamma or ex-Gaussian which often describes variation in performance with a fixed lower bound). In some embodiments, a low-performance cognitive state may be any cognitive state that is in the bottom X-th percentile of the range, where X could be any value in the range of 0-100, along the spectrum of low-performance and high-performance cognitive states. In some embodiments, a low-performance cognitive state may be defined in relation to the variability of the distribution, as in the case of a normal distribution where such states could be defined in terms of their standard deviations from the mean (e.g., performance inferior to the mean+X standard deviations, where X could be 3, 2, 1, 0, −1, −2, −3, etc.).

Enhanced performance cognitive state—In one embodiment, an enhanced-performance cognitive state is a brain state associated with supra-normal performance in a cognitive task (e.g. above normal accuracy or reaction time limits). In one embodiment, the spectrum of low-performance cognitive state(s) to enhanced-performance cognitive state(s) can be a statistical distribution (e.g. a normal distribution characterized by a mean and standard deviation, or a skewed distribution like the gamma or ex-Gaussian which often describes variation in performance with a fixed lower bound). In some embodiments, an enhanced-performance cognitive state may be any cognitive state above a high-performance state and that is in the top X-th percentile of the range, where X could be any value in the range of 0-100. In some embodiments, an enhanced-performance cognitive state may be any cognitive state above a high-performance state and defined in relation to the variability of the distribution, as in the case of a normal distribution where such states could be defined in terms of their standard deviations from the mean (e.g., performance exceeding the mean+X standard deviations, where X could be 3, 2, 1, 0, −1, −2, −3, etc.)

Contributor—In one embodiment, a contributor is a user that supplies brain signals in association with a cognitive task to facilitate creation of one or more biomarkers.

Recipient—In one embodiment, a recipient is a user that receives electrical stimulation based on the one or more biomarkers from one or more contributors.

User—In one embodiment, a user is either a contributor or a recipient.

III. System Overview

Figure 2:
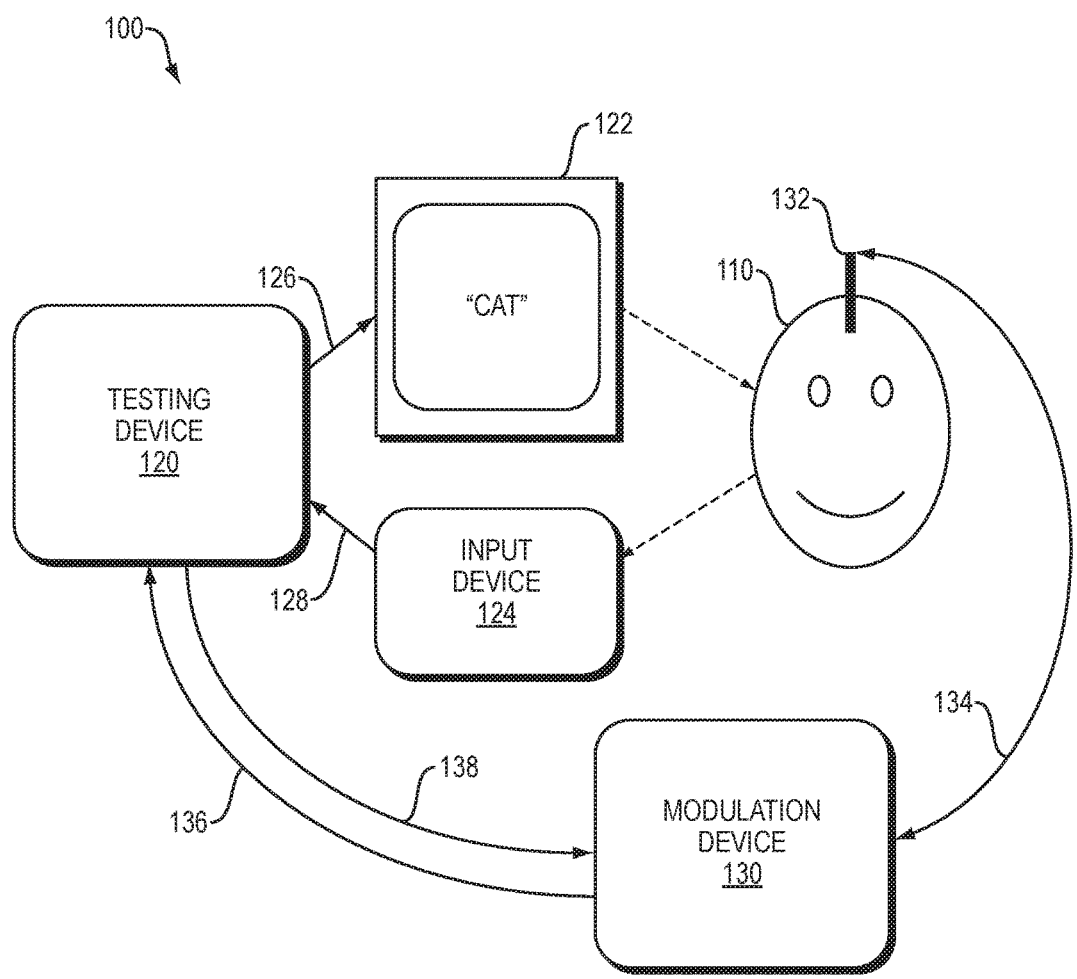
FIG. 2 is a conceptual diagram illustrating an exemplary system that can monitor brain signals and/or deliver stimulation to a user to improve brain functionality of the user according to at least one embodiment of the invention.

FIG. 2 is a conceptual diagram illustrating an exemplary system 100 that can monitor brain signals and/or deliver stimulation to a user 110 to improve brain functionality of the user 110 according to at least one embodiment of the invention. System 100 may include a testing device 120 configured to present a cognitive test to a user 110. System may also include modulation device 130 configured to monitor brain signals from a user 110 and/or deliver stimulation to a user 110 based on biomarkers identified from the cognitive test results.

Testing device 120 is configured to conduct a cognitive test on a user 110 in at least one of the two phases described herein. In the first phase, known as the testing phase, user 110 may represent one or more biomarker contributors. In the second phase, known as the modulation phase, user 110 may represent one or more recipients. In some embodiments, user 110 may be a contributor and a recipient. In some embodiments, a contributor and a recipient may be different users.

In one embodiment, testing device 120 is a computing device including a processor and memory that includes instructions that, when executed, cause the processor to implement the cognitive test. Examples of computing devices may include personal computers and smart phones, among others.

Testing device 120 may further include one or more human-machine interfaces, such as sensory interface 122 and/or input device 124 to aid in conducting the cognitive tests.

Testing device 120 may further include a communication interface to transfer data between testing device 120 and modulation device 130. Examples of communication interfaces may include a modem, a network interface (such as an Ethernet card), a communication port, a Personal Computer Memory Card International Association (PCMCIA) slot and card, etc. Data transferred via the communication interface may be in the form of signals, which may be electronic, electromagnetic, optical, or other signals capable of being transmitted or received by communication interface.

In one embodiment, the cognitive test includes one or more stimuli and one or more responses. In one embodiment, a cognitive test invokes variability in cognitive performance when user 110 performs this task. In one embodiment, stimuli are instructions posed to user 110 for performing a cognitive task (e.g., remember a word). In one embodiment, responses are provided by user 110 in response to stimuli (e.g., recalling a word user 110 was asked to remember).

In the testing phase, one or more stimuli may be presented to user 110 via sensory interface 122. One example of a stimulus may involve the presentation of a word that the user 110 is asked to remember. In alternative embodiments, a stimulus may be based on sight, sound, touch, taste or smell. For example, instead of presenting words, the stimulus may be a symbol or picture. Alternatively, the stimulus might be a certain sound or smell that the contributors are asked to remember and later recall, recognize, or produce some other memory judgment on the target item.

Sensory interface 122 may be configured to communicate information from testing device 120 to user 110 via communication link 126. While sensory interface 122 in FIG. 2 is a graphical user interface showing the word "cat" (i.e., a stimulus) for a cognitive test, other human-machine interfaces may be used to communicate the cognitive test from testing device 120 to user 110. For example, output device 112 may be a speaker or a device to test touch, smell or taste.

Communication link 126 may communicate stimulus data from testing device 120 to sensory interface 122 via a wired or wireless connection using standard communication protocols.

Input device 124 may be configured to process responses for the cognitive test from user 110. Examples of input devices may include a keyboard, mouse, joystick, touch screen, microphone, an eye fixation tracking device and/or a stylus. The responses may be necessary to verify whether the user 110 performed the cognitive task. For example, it may not be known whether a word is remembered or forgotten by a user 110 until s/he is prompted to remember each word and provide a response at a later time. If the response matches the stimulus, then user 110 (e.g., a contributor) may be in an enhanced-performance or high performance cognitive state. If the response does not match the stimulus, then user 110 (e.g., a contributor) may be in a low-performance cognitive state.

Communication link 128 may communicate response data received by input device 124 to testing device 120 via a wired or wireless connection using standard communication protocols.

Modulation device 130 may be configured to monitor electrical, magnetic and/or chemical brain signals of user 110 and/or deliver electrical, magnetic and/or chemical stimulation to brain regions of the brain of user 110. It should be noted that in view of the teachings herein, one of skill in the art understands that modulation device 130 can in certain instances both sense brain signals and stimulate parts of the brain. In one embodiment, modulation device 130 is a deep brain stimulation device. In one embodiment, modulation device 130 is ACTIVA® PC+S, developed by Medtronic, Inc. In one embodiment, modulation device 130 is RNS® System, developed by NeuroPace, Inc. One embodiment of the modulation device 130 is described in more detail in FIG. 5.

Modulation device 130 may further include one or more electrodes, such as electrode 132, which are implanted in the brain of user 110. The one or more electrodes sense the electrical signals in the brain that are provided to modulation device 130 via lead 134.

In one embodiment, modulation device 130 may be configured to monitor brain signals of user 110 during the cognitive test and, optionally, provide monitored brain signal data (i.e. first monitored brain signal data) of user 110 to testing device 120 via communication link 136.

Communication link 136 may communicate the monitored brain signal data received by modulation device 130 to testing device 120 via a wired or wireless connection using standard communication protocols.

Using the stimulus data, the response data and monitored brain signal data, testing device 120 may process the data to identify biomarkers indicative of an enhanced-performance cognitive state, a high-performance cognitive state or a low-performance cognitive state of the user 110 and generate biomarker data. Biomarker data may be transmitted from testing device 120 to modulation device 130 using communication link 138. In alternative embodiments, modulation device 130 may identify biomarkers using the stimulus data, the response data and/or monitored brain signal data of the user 110 that can later be used to determine how to deliver stimulation to the brain of user 110. In this embodiment, stimulus data and/or response data may be transmitted from testing device 120 to modulation device 130 using communication link 138.

Communication link 138 may communicate the biomarker data, the stimulus data and/or the response data from testing device 120 to modulation device 130 via a wired or wireless connection using standard communication protocols. In an alternative embodiment, communication link 136 and communication link 138 may be one bi-directional communication link.

In one embodiment, modulation device 130 may receive the biomarker data, the stimulus data and/or the response data from testing device 120, may store the data in memory associated with modulation device 130. In one embodiment, modulation device 130 may receive the stimulus data and/or the response data and generate the biomarkers before storing the biomarkers in memory.

In the modulation phase, in association with a cognitive test presented to a user 110 (e.g., recipient) by testing device 120, modulation device 130 may receive monitored brain signal data from user 110. Modulation device 130 may then compare the monitored brain signal data (i.e., second monitored brain signal data) to a biomarker and deliver certain stimulation to the brain of the user 110 based on the biomarker and the monitored brain signal data. In some embodiments, modulation device 130 may generate a modulation phase biomarker from the monitored brain signal data (i.e., second monitored brain signal data) to compare to the biomarker generated during the testing phase (i.e. testing phase biomarker).

In various embodiments, certain stimulation may be delivered by modulation device 130 to a brain of user 110 targeted for maintaining an enhanced or a high-performance cognitive state if the brain signals indicate an enhanced or a high-performance cognitive state is present in the brain of user 110. Alternatively, certain stimulation may be delivered by modulation device 130 to a brain of user 110 targeted for creating an enhanced or high-performance cognitive state if the brain signals indicate the presence of a low-performance cognitive state in the brain of user 110.

In various embodiments, modulation device 130 includes a plurality of leads (e.g., lead 134) including a plurality of electrodes (e.g., electrode 132). In various embodiments, certain brain signals may be monitored by one or more electrodes of one or more leads. In various embodiments, electrical stimulation may be delivered to one or more electrodes of one or more leads to drive the brain of user 110 to an enhanced or high performance cognitive state.

In alternative embodiments, testing device 120 and/or modulation device 130 may include different combinations of functions, software and/or hardware as described in system 100 and the document herein. In alternative embodiments, different testing devices (e.g. testing device 130) may be used to present cognitive tests to one or more contributors and/or one or more users. In alternative embodiments of the invention, different modulation devices (e.g., modulation device 130) may be used to monitor brain signals of one or more contributors and/or one or more users. In alternative embodiments, different modulation devices (e.g., modulation device 130) may be used to deliver stimulation to neurons of the brain of one or more users. In some embodiments, system 100 may implement the testing phase and/or the modulation phase as described herein.

IV. Testing Phase

Figure 3:
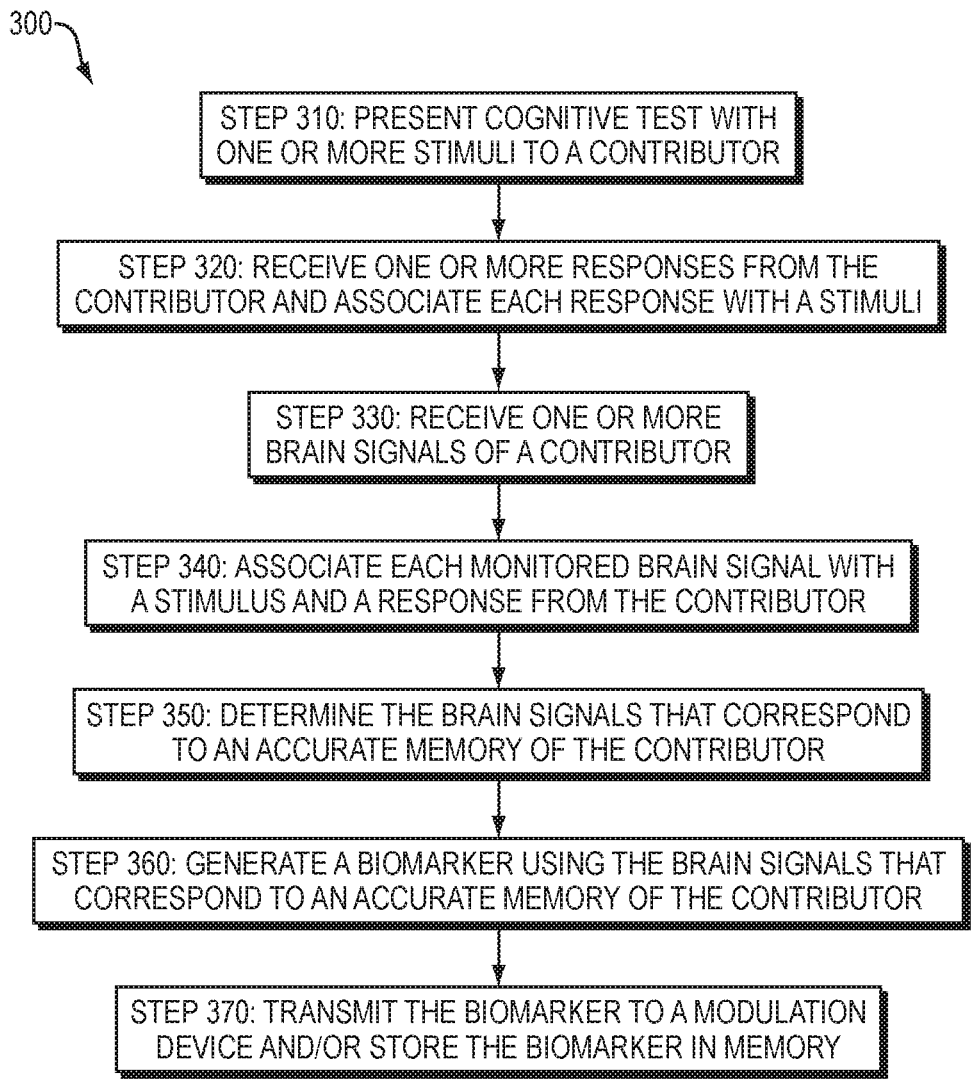
FIG. 3 illustrates a flow chart of a method for creating a biomarker indicative or associated with a desired state of performance of a given user for a given cognitive task according to at least one embodiment of the invention.

FIG. 3 illustrates a flow chart of a method 300 for creating a biomarker indicative or associated with a desired state of performance of a given user for a given cognitive task according to at least one embodiment of the invention.

At step 310, a cognitive test may be presented to one or more contributors (e.g. user 110) using testing component 120. In one embodiment, the cognitive test includes a cognitive task (e.g., memory game) to be performed by one or more contributors.

In one embodiment, the cognitive test may include one or more stimuli and require one or more contributor responses. First, one or more stimuli may be presented to the one or more contributors. In one embodiment, the one or more stimuli are presented to the one or more contributors via sensory interface device 122, as described herein. In one example of a cognitive test, a contributor might be asked to remember, and later recall, twelve words. After the test, the contributor might remember six of the words and forget the other six words.

At step 320, testing device 120 may receive one or more responses from the contributor and may associate each response with a stimulus. In one embodiment, the response is received from the contributor via input device 124, as described herein. In one embodiment, testing device 120 may associate each response with a stimulus by matching the response to the stimulus. For example, if the contributor is asked to remember a set of twelve words, the contributor might recall six of the words. If one of the presented words is "cat" and the contributor provides a response of "cat" using input device 124, testing device 120 may match the two words together using a standard comparison technique. In this instance, if the response matches the stimulus, testing device 120 may determine that a positive response was provided to testing device 120 from the contributors for the stimulus and associate the positive response with the stimulus. For the six words that the contributor cannot recall or where a response is provided that does not match any of the stimuli, testing device 120 may determine that a negative response was provided to testing device 120 from the contributor and associate the negative response with the stimulus. Other quantitative indices of performance that may be used to define biomarkers include measures of the dynamics of recall including clustering on the basis of temporal, semantic and spatial similarities among items, inter-response times, and the similarity of error responses to the target items in the studied list. In an alternative embodiment, a contributor may be presented with a virtual environment through the sensory interface 122 and be instructed to navigate to particular locations indicated by visual landmarks ("the target"). The contributor may later be asked to navigate to those locations without the presence of the landmark. The contributor's performance may then be characterized as high-performance or low-performance depending upon how close to the target they got and how long it took them to travel to the target location.

At step 330, during the time period around when each stimulus is presented to the contributor, one or more brain signals of the one or more contributors may be monitored and received by modulation device 130 via one or more electrodes (e.g., electrode 132) implanted within the brain of the contributor. The brain signals may be subsequently received by testing device 120 after transmission by modulation device 130.

At step 340, testing device 120 may associate each of the monitored brain signals with a corresponding stimulus. In one embodiment, testing device 120 associates the stimulus and the monitored brain signal by comparing a time period where modulation device 130 monitored the brain signals to a time period when the stimulus was presented to a contributor by testing device 120. If the time periods overlap, then testing device 120 associates the monitored brain signals with the stimulus. For example, the testing device 120 may display a stimulus such as the word "cat" on a display to a contributor from a time t to a time t+5 seconds and then may display the word "dog" on a display to a contributor from a time t+6 seconds to a time t+11 seconds. In conjunction, modulation device 130 may monitor brain signals from time t to time t+11 seconds. Testing device 120 may be configured to associate all brain signals from time t to time t+5 seconds with the stimulus using the word "cat" and associate all brain signals from time t+6 seconds to a time t+11 seconds with the stimulus using the word "dog" so that testing device 120 can later be used to identify the biomarkers.

At step 350, testing device 120 may determine the one or more brain signals that correspond to an accurate memory (i.e. enhanced or high-performance cognition) or an inaccurate memory (i.e. low-performance cognition) of the contributor. In one embodiment, the one or more brain signals that correspond to a stimulus having a correct or fast response from the contributor may be considered one or more brain signals that correspond to an accurate memory state of the contributor. In some embodiments, testing device 120 may determine the one or more brain signals that correspond to an inaccurate memory of the contributor. In one embodiment, the one or more brain signals that correspond to a stimulus having an incorrect or slow response from the contributor may be considered one or more brain signals that correspond to an inaccurate memory state of the contributor.

At step 360, testing device 120 may generate one or more testing phase biomarkers using one or more brain signals that correspond to an accurate memory of the contributor and/or the brain signals that correspond to an inaccurate memory of the contributor. The one or more testing phase biomarkers may be generated from the received brain signals based on one or more characteristics that distinguish one or more brain signals corresponding to enhanced or high-performance cognition from one or more brain signals corresponding to low-performance cognition. Further, the one or more testing phase biomarkers may be generated from the received one or more brain signals because the one or more brain signals corresponding to an accurate memory (i.e. enhanced or high-performance memory cognition) may share a first set of one or more common characteristics that are distinguishable from one or more brain signals corresponding to an inaccurate memory (i.e. low-performance memory cognition) that may share a second set of one or more common characteristics. For example, the one or more testing phase biomarkers might be based on patterns that emerge in the one or more brain signals, such as energy content within a particular bioelectrical frequency band, morphological patterns, consistent period of oscillation, and/or changes in bioelectrical amplitude or frequency, for example. In addition, the testing phase biomarker might be based on a similar frequency, bioelectrical oscillation frequency-band power, and/or phase of oscillation of the brain signals that correspond to an accurate memory of the contributor.

In one embodiment, a testing phase biomarker may correspond to one or more brain signals from different populations of neurons or brain regions over one or more time periods (i.e. a spatio-temporal biomarker). FIG. 6 illustrates an example of electrical activity in a brain while a contributor is attempting to accurately create a memory over time according to at least one embodiment of the invention. Each row of brain images represents a visual depiction of the electrical activity in the brain of a contributor during a certain time period. For example, the first row of brain images represent the brain of the contributor at −750 ms to 250 ms, the time period before and immediately after a stimulus (e.g. a word shown on a visual display) has begun to be shown to a contributor. "Word on" represents when a word is first shown to a contributor while "word off" represents when a word is no longer shown to a contributor. The second through fifth rows of brain images represent the brain of the contributor from 0 ms to 1700 ms (i.e. the period when the contributor is shown a stimulus). The seventh row of brain images represent the brain of the contributor at 1600 ms to 2100 ms (i.e. the period immediately preceding when the contributor is no longer shown the stimulus to the period after the contributor is shown the stimulus). As time progresses, different brain areas are activated as the contributor attempts to accurately create a memory, as reflected in the increase in high-frequency activity measured from intracranially implanted electrodes in that region. Here, statistically reliable memory encoding related high-frequency signals, which have been shown to correlate positively with neuronal spiking, appear as grayscale shading overlaying different areas of the brain. The signals measured in these areas of the brain (e.g., the high frequency activity in FIG. 6) that reliably predict the goodness of memory function based on their correlation with stimulus encoding events and subsequent memory performance constitute a particular biomarker of good memory encoding in the contributor. Individual biomarkers, such as these, combine mathematically to create multivariate indices of memory function which we refer to more generally as testing phase biomarkers in the subsequent sections. Note that testing phase biomarkers refer to biomarkers generated during an assessment of cognitive function, and that these biomarkers may be uniquely determined for different aspect of cognitive performance such as memory encoding, memory retrieval, reinstatement of the context of previously learned information, or cognitive operations that are crucial for perception, attention, learning, memory or decision making.

In one embodiment, a testing phase biomarker may correspond to one or more brain signals from one or more brain regions. FIG. 7 illustrates an example of the brain's electrical activity as a contributor is attempting to accurately create a memory according to at least one embodiment of the invention. In this embodiment, the biomarker is only spatio-dependent, meaning dependent on the location of the neurons, and not the time period when the neurons are activated, are needed to create a biomarker. Here, neural activity, which is significantly correlated with memory performance, is shown using grayscale shading. For these significant areas of the brain of a contributor, one or more characteristics of the brain signals are analyzed and correlated to create a testing phase biomarker. These brain signals may be weighted, correlated and/or combined using different signal processing techniques to create a testing phase biomarker.

In some embodiments, testing device 120 may generate one or more biomarker representative values. If a large set of testing phase biomarkers is identified, the set may be reduced to a one or more biomarker representative values using one or more dimensionality reduction algorithms (such as linear classifiers, support vector machines, neural networks, etc.) to classify the brain signals into enhanced-performance cognition, high-performance cognition and low-performance cognition states. In some embodiments, each of the one or more biomarker representative values may correspond to a value along a range (e.g., 0 to 1). In these embodiments, certain values along the range may correspond to low-performance cognition (e.g., 0), high-performance cognition (e.g., 0.5) and enhanced-performance cognition (e.g., 1).

In some embodiments, testing device 120 may generate one or more stimulation optimization parameters corresponding to one or more biomarkers or biomarker representative values. In some embodiments, the electrical stimulation parameters may be optimized during a stimulation optimization phase. In these embodiments, one or more electrical stimulations may be sequentially applied to the biomarker recipient's brain at varied locations and using varied stimulation parameters (such as amplitude, frequency, pulse width, etc.) to determine the effects of each parameter set on the set of testing phase biomarkers or biomarker representative values. In some embodiments, the stimulation locations and signal parameters for subsequent electrical stimulation during the modulation phase are chosen in the stimulation optimization phase based on the degree to which one or more stimulation locations and parameters produce a desired effect on the recipient's brain, such as causing a match (e.g., correlation) between the recipient's brain signals during the stimulation optimization phase and the set of biomarkers or biomarker representative values identified in the testing phase to improve memory.

This stimulation optimization phase can be repeated as often as needed to optimize the effectiveness of the modulation phase in improving the recipient's cognitive performance. For example, the recipient's cognitive performance may change over time. In response, the stimulation optimization phase may be repeated to adjust the electrical stimulation parameters to cause the desired effect on the recipient's brain.

Turning back to FIG. 3, at step 370, the testing phase biomarker may be transmitted from testing device 120 to modulation device 130, where the testing phase biomarker may be stored in memory of the modulation device 130. In some embodiments, the biomarker representative values and/or stimulation optimization parameters may be transmitted from testing device 120 to modulation device 130. Testing device 120 may also store the testing phase biomarker, biomarker representative values and/or stimulation optimization parameters in memory (e.g. a database) for subsequent us by others, including modulation device 130.

In alternative embodiments, modulation device 130 may include one or more components of testing device 120 to implement the method 300. In alternative embodiments, modulation device 130 may generate testing phase biomarkers using the stimulus data, the response data as well as monitored brain signal data. In these embodiments, stimulus data and response data is transmitted from testing device 120 to modulation device 130. In these embodiments, modulation device 130 may receive the stimulus data and/or the response data and may generate the testing phase biomarkers before storing the testing phase biomarkers in memory.

The testing phase biomarkers will be used during a subsequent or second cognitive test presented to a recipient to determine whether the subsequently or second monitored brain signal data (e.g., modulation phase biomarker) correspond to an accurate memory of the contributor and whether modulation device 130 will need to deliver stimulation to the brain of the recipient as described for FIG. 4. It would be readily apparent to anyone skilled in the art that data collected in this subsequent testing phase can be used to further refine the biomarkers. This later phase could thereby be used to "tune" the stimulation parameters to the biomarkers as they may drift over time.

V. Modulation Phase

Figure 4:
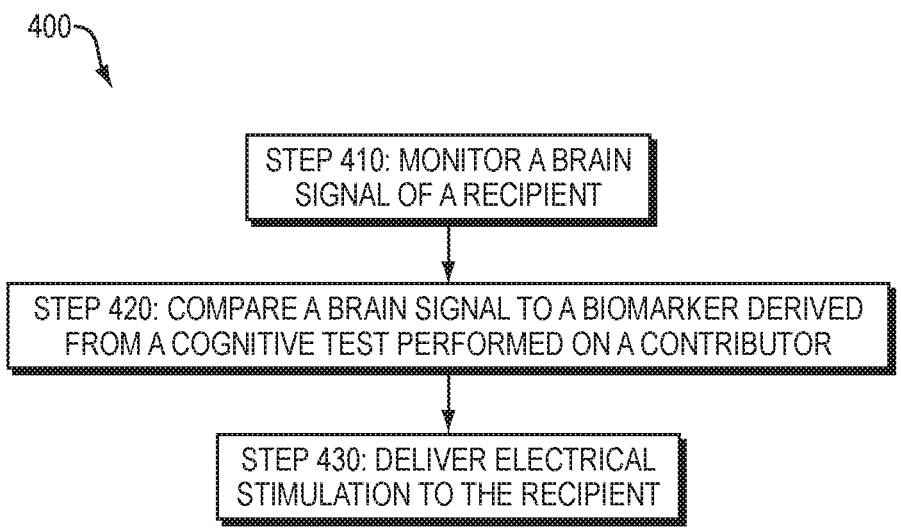
FIG. 4 illustrates a flow chart for delivering stimulation to improve cognition (e.g.

FIG. 4 illustrates a flow chart 400 for delivering stimulation to improve cognition (e.g. memory cognition) according to at least one embodiment of the invention.

At step 410, modulation device 130 may monitor a brain signal of the recipient (e.g., user 110). In one embodiment, modulation device 130 may monitor a brain signal of the recipient via one or more electrodes (e.g., electrode 132) implanted within the brain of the recipient.

In some embodiments, a plurality of brain signals may be monitored by modulation device 130. In various embodiments, a brain signal may be indicative of neural activity. In various embodiments, a modulation device 130 may measure a brain signal of a brain region.

In some embodiments, modulation device 130, or another device, may identify and/or derive modulation phase biomarkers using the brain signals monitored by modulation device 130 during the modulation phase.

At step 420, modulation device 130 may compare the one or more brain signals, or modulation phase biomarkers, to one or more testing phase biomarkers derived from a cognitive test performed on a contributor as described herein. In one embodiment, the brain signal is compared to a testing phase biomarker indicative of an enhanced or high-performance cognition as determined based on a cognitive test performed on a contributor. In another embodiment, the brain signal is compared to a testing phase biomarker indicative of low-performance cognition as determined based on a cognitive test presented to a contributor. In one embodiment, modulation device 130 may retrieve one or more testing phase biomarkers stored in memory of modulation device 130 and/or testing device 120.

In one embodiment, a testing phase biomarker is a threshold corresponding to a characteristic of a brain signal corresponding to an enhanced or high-performance cognition or a brain signal corresponding to low-performance cognition. If the testing phase biomarker is a threshold biomarker, the stimulation may be triggered for the recipient if the brain signals of the recipient indicate transition from an enhanced or high-performance cognition to low-performance cognition, or vise versa. Alternatively, if the testing phase biomarker is a threshold biomarker, the stimulation may be triggered for the recipient under the condition that the brain signals of the recipient indicate that the recipient is maintaining enhanced or high-performance cognition or low-performance cognition.

In some embodiments, modulation device 130 may compare the one or more brain signals, or modulation phase biomarkers, to one or more biomarker representative values derived during the testing phase, as described herein. In some embodiments, modulation device 130 may first derive modulation phase biomarker representative values and compare these biomarker representative values to the biomarker representative values derived during the testing phase.

At step 430, modulation device 130 may deliver certain stimulation (e.g., electrical, chemical, magnetic) to the brain of the recipient based on the comparison of the brain signal determined during the modulation phase to one or more testing phase biomarkers (or alternatively, based on the comparison between the modulation phase biomarker representative values and the testing phase biomarker representative values). In one embodiment, modulation device 130 may deliver certain electrical stimulation to the brain of the recipient via the one or more electrodes (e.g., electrode 132).

In various embodiments, certain stimulation may be delivered by modulation device 130 to a brain of a recipient targeted for maintaining enhanced or high-performance cognition if the brain signals indicate enhanced or high-performance cognition of the brain of the recipient. In various embodiments, certain stimulation may be delivered by modulation device 130 to create enhanced or high performance cognition if the brain signals indicate low-performance cognition of the brain of the recipient, or vice versa. For example, the stimulation may transition the brain of the recipient from a low performance cognitive state to an enhanced or high-performance cognitive state, or vice versa.

In some embodiments, modulation device 130 may deliver certain stimulation based on the stimulation optimization parameters determined during the stimulation optimization phase, described herein.

In some embodiments, delivering stimulation to the brain of the recipient may be user-specific. For example, the modulation device 130 may stimulate the brain in one recipient using different parameters from those used to stimulate the brain of a second recipient. Because of these user-specific differences in the effect of delivered stimulation, in some instances, where stimulation is applied to a recipient that does not realize the full effect of the stimulation, the stimulation may not create or maintain enhanced or high-performance cognition in the brain of the recipient. To properly provide adequate stimulation, modulation device 130 may adjust stimulation applied to the brain of the recipient to achieve a desired result (e.g., maintain enhanced or high-performance cognition) based on predetermined user-specific parameters. In some embodiments, modulation device 130 may first apply stimulation to a recipient using an initial set of stimulation parameters (such as frequency, pulse width, amplitude, etc.), monitor the physiological results of stimulation and determine a new user-specific set of stimulation parameters by comparing the results of stimulation with the desired enhanced- or high-performance brain state. This process may be repeated on an ongoing basis during the modulation phase, as it is possible that a response of a recipient to stimulation may vary over time.

In alternative embodiments, the testing phase described in method 300 may overlap with the modulation phase described in method 400. If the phases overlap, then monitored brain signal data of a recipient and the corresponding responses of the recipient to stimuli can be used to update the one or more testing phase biomarkers generated in step 360.

In some embodiments, the contributor is the same user as the recipient. By having the same user act as a contributor and a recipient, system 100 may allow for real-time or contemporaneous updates to a testing phase biomarker as stimulation is also applied to the user. In some embodiments, the contributor and the recipient are different users. By having different users as contributors and recipients, potential recipients will not need to experience a testing phase before using the device to alter cognition, thereby saving time for the future recipients.

In some embodiments, modulation device 130 delivers stimulation to a recipient without first determining the current brain signal pattern/state of the recipient. In this way, the recipient's current brain signals can be overridden based on a biomarker to thereby alter the brain signal pattern/state of the recipient without first waiting to determine the current brain signal pattern/state of the recipient.

V. Description of Sensing and Modulation Device

FIG. 5 is a functional block diagram illustrating components of modulation device 130 according to at least one embodiment of the invention. In this embodiment, modulation device 130 includes control circuitry components including processor 240, memory 241, stimulation generator 242, sensing module 244, switch module 246, communication module 248, and power source 250.

Memory 241 may include any volatile or non-volatile media, such as a random access memory (RAM), read only memory (ROM), non-volatile RAM (NVRAM), electrically erasable programmable ROM (EEPROM), flash memory, and the like. Memory 241 may store computer-readable instructions that, when executed by processor 240, cause modulation device 130 to perform various functions described herein. Memory 241 may include operating instructions 256 executable by the processor 240 for causing modulation device 130 to carry out the functions referenced herein. Memory 241 may store stimulation instructions as part of stimulation programs 252 that are available to be selected by processor 240 in response to detection of brain signals from the sensing module 244 and a comparison of the brain signals to testing phase biomarkers stored in cognitive test data 253. In addition, processor 240 may be configured to record diagnostic information, such as sensed signals, signal characteristics, brain state episode information, or the like in memory 241 or another memory or storage device. The various functions and options described herein may be performable automatically by modulation device 130 by processor 240 execution of operating instructions 256, cognitive test data 253 and/or stimulation programs 252 stored in memory 241.

The steps, procedures, techniques, etc. referenced herein may be carried out in part by, for example, software instructions, such as those used to define a software or computer program. The computer-readable medium (e.g., memory 241) may store instructions (e.g., operating instructions 256, cognitive test data 253 and stimulation programs 252) executable to carry out the steps, procedures, techniques, etc, described herein.

Processor 240 may determine whether a monitored brain signal includes a biomarker (e.g., testing phase biomarker or modulation phase biomarker) indicative of enhanced-performance, high-performance or low performance cognition by comparing the brain signal to a testing phase biomarker stored in cognitive test data 253. Processor 240 may analyze a monitored brain signal for correlation with a template, or a specific stored value. For example, the peak, lowest or average amplitude of the brain signal may be compared to a threshold, the crossing of the threshold indicating a new presence of enhanced-performance, high-performance or low performance cognition.

Processor 240, as part of control circuitry, may be configured to control stimulation generator 242 to deliver stimulation based on the results of monitoring the brain signals. Processor 240, may be configured to control simulation generator 242 to deliver stimulation with pulse voltage or current amplitudes, pulse widths, and frequencies (i.e., pulse rates), and electrode combinations specified by the stimulation programs 252 with predetermined delays, e.g., as stored in memory 241. In some embodiments, processor 240 may control stimulation generator 242 to deliver a substantially continuous stimulation waveform rather than pulsed stimulation. In various embodiments, one or more parameters of the stimulation may be changed according to the comparison between the testing phase biomarker and the second monitored brain signal data. Changing one or more parameters can include changing the energy level of the stimulation, such as by adjusting frequency, amplitude, and/or duration of one or more pulses comprising the stimulation. Other parameters that can be changed include adjusting the timing of a stimulation window or other timing parameter for delivery of stimulation.

Processor 240, may include any of one or more of a microprocessor, a controller, a digital signal processor (DSP), an application specific integrated circuit (ASIC), one or more gate arrays (e.g., a field-programmable gate array (FPGA)), discrete logic circuitry, and any number of each. The functions attributed to the control circuitry and/or a processor may be embodied as firmware, hardware, software or any combination thereof specifically configured (e.g., with programming) to carry out those functions.

Sensing module 244 is configured to sense brain signals of user 110 (shown in FIG. 2) via a selected subset of the set of electrodes 132, or with one or more electrodes of the set of electrodes 132. Processor 240 may control switch module 246 to electrically connect sensing module 244 to a selected subset of the set of electrodes 132, or with one or more electrodes of the set of electrodes 132. In this way, sensing module 244 may selectively sense bioelectrical brain signals with different combinations of one or more electrodes. Although the electrodes 132 are principally described as being implanted within a brain in the manner of DBS, other locations are additionally or alternatively contemplated. For example, electrodes 132 may be deployed at selected tissue sites or on selected surfaces of a human patient, such as on the brain, along the cortex, proximate the spinal cord, on the scalp, or elsewhere. As an example, scalp electrodes may be used to measure or record EEG signals. As another example, electrodes implanted at the surface of the cortex may be used to measure or record ECoG signals. In some embodiments, an external device may be worn with sensing elements positioned at a desired location adjacent the patient to detect a physiological signal (e.g., a brain signal).

Sensing module 244 may form part of a sensor circuit configured to monitor a variety of signals via a variety of different sensing elements, such as a brain signals via electrodes 132 and/or other physiological signals. In some embodiments, sensing module 244 includes circuitry configured to measure one or more parameters of a brain signal, such as amplitude, frequency or phase. Processor 240 may compare the measured parameters of the brain signal (e.g., modulation phase biomarker) to a testing phase biomarker stored in cognitive test data 253. For example, processor 240 may determine whether the measured parameters of the brain signal exceeds or falls below a threshold representative of the testing phase biomarker.

Processor 240 or other part of control circuitry may monitor brain signals sensed by sensing module 244 in any suitable manner in order to detect and characterize enhanced or high-performance cognition or low-performance cognition. For example, sensing module 244 may sense one or more brain signals (e.g., a LFP (local field potential), neural firings, chemical changes in the brain) at one or more particular points within a portion of the brain of user 110 that supports enhanced or high-performance cognition or low-performance cognition, and processor 240 may monitor the brain signals. In one embodiment, processor 240 can monitor brain signals and determine stimulation for user 110 in real-time to maintain enhanced or high performance cognition for user 110 based on a comparison of modulation phase biomarker derived from monitored brain signals) to a testing phase biomarker.

Electrodes 132 can be used by sensing module 244 to sense the one or more brain signals. The set of electrodes 132 of lead 134 may include one or more of electrodes 132A, 132B, 132C, 132D, 132E, 132F. In one embodiment, the number of electrodes (N) may be any whole number. In one embodiment, N may be one of: one, two, three, four, five, six, seven, eight, nine, and ten. In one embodiment, N may be more than one and less than one hundred. In one embodiment, N may be more than one hundred and less than one thousand. In one embodiment, N may be more than one thousand and less than ten thousand.

Processor 240 may control switch module 246 to deliver electrical stimulation signals generated by stimulation generator 242 to each electrode of the set of electrodes 132. Processor 240 may control switch module 246 to monitor brain signals from each electrode of the set of electrodes 132 using sensing module 244.

In one embodiment, modulation device 130 includes a plurality of leads (e.g., lead 134). In one embodiment, each lead of the plurality of leads includes a set of electrodes (e.g., set of electrodes 132). In one embodiment, lead 134 may include any combination of electrodes 132, such as mesoscale electrodes (e.g., 132A, 132B, 132C, 132D) or radial electrodes (e.g., 132E, 132F). Examples of different electrodes are described in PCT Application No. PCT/IL02/00796, titled "Electrode System for Neural Applications," and incorporated by reference herein in its entirety. In one embodiment, electrode 132 includes one or more grid electrodes provided on the surface of the brain of user 110. In one embodiment, electrode 132 is an intra-cranial electrode (e.g., hippocampus electrode) that measures one or more brain signals of the hippocampus. In one embodiment, at least one of the electrodes 132 is sized to sense a subfield of a brain region (e.g., hippocampus). In one embodiment, a first lead of a plurality of leads may be positioned in a first brain region of user 110 and a second lead of a plurality of leads may be positioned in a second brain region of user 110.

In various embodiments, certain electrical stimulation may be delivered to certain electrodes of certain leads. In these embodiments, each lead includes one or more sub-leads to individually connect one or more electrodes to processor 240. In various embodiments, electrical stimulation is delivered to neurons of the brain of user 110. In various embodiments, electrical stimulation is delivered to a single subfield of a hippocampus. In various embodiments, electrical stimulation is delivered to multiple regions of the brain of user 110 simultaneously.

In one embodiment, mesoscale electrodes are spaced on a lead to maximize conductive surface area of the portion of the lead implanted in the brain of user 110. Such a configuration may maximize the number of brain areas that can be monitored and/or stimulated by modulation device 130.

In various embodiments, modulation device 130 may include one or more external electrodes positioned on the outer surface of the cranium of user 110 that can sense and generate a bioelectrical brain signal that can be used to detect and characterize a brain signal of user 110. Such detection and characterization may use the techniques discussed herein for detecting and characterizing via internally sensed signals (e.g., comparing signals, frequency or other parameter match, a biomarker, template, and/or other technique).

In various embodiments, modulation device 130 may include a transcranial magnetic module, connected to and controlled by processor 240 to sense or stimulate electrical signals in the brain of user 110 via magnetic induction for similar purposes as described herein.

Communication module 248 may support wired or wireless communication between modulation device 130 and testing device 120. Processor 240 may receive, as updates to sensing and/or stimulation programs, values for stimulation parameters such as amplitude and electrode combination information from testing device 120, stimulus data and response data related to a cognitive test, via communication module 248. The updates to the stimulation, sensing, or other programs may be stored within stimulation programs 252 of memory 241. Stimulus data and response data may be stored in cognitive test data 253. In one embodiment, modulation device 130 generates a testing phase biomarker using the monitored brain signals, stimulus data and response data during the testing phase using the methods, functions and/or components described herein. In one embodiment, modulation device 130 generates a modulation phase biomarker using the monitored brain signals during the modulation phase using the methods, functions and/or components described herein. Communication module 248 may send data (e.g., brain signal data) to testing device 130 on a continuous basis, at periodic intervals, or upon request from testing device 130.

Power source 250 may deliver operating power to various components of modulation device 130.

VI. Results

FIG. 8 illustrates an exemplary graph of potential performance improvement that can be gained from biomarkers at various time points and frequencies according to at least one embodiment of the invention. In this example, the scale bar on the right of the graph represents the percentage improvement that can be gained using the techniques and devices described herein. In this example, the percentage improvement may range from zero to sixty. As shown in this example, when the devices and techniques described herein are used at certain times and/or frequencies, certain improvements can be achieved. For example, at region 802, centered around time 850 ms at a frequency of 4 Hz, a 60% improvement in accurately creating memories was realized in users.

FIG. 9 illustrates potential performance gains available by reinstating the biomarkers associated with various quartiles of performance according to at least one embodiment of the invention. This figure identifies the potential performance gains that it is possible to obtain using an embodiment of the one or more devices and methods described in this patent application. These gains, such as the change from 1st quartile to 4th quartile showing approximately 100% improvement, are illustrative of the potential gains realized using one or more of the devices and methods described herein.

VII. Example

Human episodic memory is dynamic, leading to satisfying periods of good memory as well as frustrating momentary lapses. Neural mechanisms that are engaged when memoranda are encountered lead to encoding of memory representations in the brain. These mechanisms vary in their efficiency, which leads to variability in the likelihood of remembering information later on. Here, some embodiments describe use of targeted electrical stimulation of the human brain to modulate neural activity at encoding. In these embodiments stimulation's effect is measured on neural activity and use it to predict stimulation's effect on subsequent memory performance. Intracranial recordings are first collected while neurosurgical patients studied lists of words for a later recall test. Using multivariate classification of neural activity, a model is fitted that could discriminate between words likely to be later remembered vs. forgotten, and is applied to data collected in later stimulation sessions. When neural activity indicated recall was unlikely to be successful, stimulation improved performance, while the reverse was true when recall was predicted to be successful. The stimulation-evoked change in the probability of memory success, estimated from neural activity, correlated with the stimulation-evoked change in memory performance. These findings indicate that memory success can be decoded from multivariate neural activity and can be predictably modulated with electrical stimulation. The data suggest that electrical stimulation-based interventions could be used to therapeutically modulate memory dysfunction.

Memory function depends on encoding processes that lay down representations of our experiences for long term storage, but these processes vary in their efficiency from moment to moment. Recordings of neural activity taken during encoding show that the response in many brain areas differentiates information that is likely to be later remembered from information likely to be forgotten. These differences have been observed in subcortical areas such as the hippocampus as well across cortex. The presence of subsequent memory effects (SMEs) across many brain regions suggests that the coordinated activity of a distributed neural network is responsible for effective memory encoding.

If neural activity at encoding predicts variation in later memory success, then modulation of neural activity at encoding should effect subsequent memory performance. This assumption is the foundation of attempts to use electrical stimulation of the brain to affect memory performance, but it has been difficult in humans to predict memory outcomes from the neurophysiological consequences of stimulation. Non-invasive methods like transcranial direct current stimulation (tDCS) have shown the potential to influence memory performance, but have unclear neurophysiological mechanisms of action. Invasive methods such as direct intracranial stimulation of the medial temporal lobe (MTL) have yielded inconsistent behavioral effects, with some studies showing improvement and many others showing disruption. In some embodiments, neural activity collected across the brain is used and that stimulation's effect on brain-network activity would predict stimulation's effect on memory performance.

In some embodiments, the approach was to use multivariate pattern analysis (MVPA) to derive estimates of encoding efficiency from neural activity. The relation was quantified between neural activity and the efficiency of memory encoding by recording electrical signals from neurosurgical patients implanted with subdural and depth electrodes as they performed a memory task. A machine learning classifier was trained to discriminate between brain-wide patterns of neural activity that predicted later memory success from patterns that predicted later memory failure. This classifier was then tested on neural recordings collected during later independent sessions of the memory task. In these later sessions, electrical stimulation is applied to specific brain regions in order to influence network activity. Brain stimulation is predicted to modulate memory performance to the extent that it influenced physiology across the network. The classifier was used to decode neural activity recorded before and after stimulation and examined how stimulation-induced changes in encoding efficiency predicted later memory performance.

In some embodiments, intracranial electroencephalographic (iEEG) signals were recorded from electrodes implanted in the brains of 32 subjects. Subjects performed a free recall memory test during which they studied lists of 12 unrelated words followed by a 20 second mental arithmetic distractor task. Subjects were then asked to freely recall the words from the list in any order (FIG. 10$a$).

One goal was to analyze brain activity during study to derive estimates of encoding efficiency for each individual word. To this end, a logistic regression classifier was trained to discriminate between patterns of brain activity predictive of successful memory (remembering learned information following the delay) and those predictive of unsuccessful memory (forgetting of such information; FIG. 10$b$). A subset of subjects (N=23) performed additional sessions of the memory task in which we applied targeted electrical stimulation during encoding. For each session stimulation was applied across a single pair of electrodes, selecting contacts which showed a significant SME in the high-frequency range, a marker of successful memory encoding in iEEG. Stimulation to MTL and prefrontal cortical structures known to be critical for memory encoding was targeted and stimulation parameters that have previously been linked to improvements in spatial memory function in humans was used. Each patient's unique classifier trained on the record-only sessions was used to decode encoding efficiency from neural activity during stimulation sessions.

Subjects completed at least 25 unique free recall lists during each of the record-only sessions (mean recall=27.4±2.1%; standard error of the mean, SEM; FIG. 10$a$). To train the classifier, spectral decomposition of the iEEG signal recorded at each electrode was used to estimate power in time-frequency space for each word presentation period (1600 ms; FIG. 10$b$, top panel). The power spectrum was then averaged across the time dimension and sorted individual word events into recalled and forgotten bins. Leave-one-out cross validation by word list was used to train the classifier to discriminate recalled patterns from forgotten patterns. Area under the curve (AUC) was used to assess classifier performance and the AUC values were compared for each subject to a subject-specific null distribution. Data from two example subjects are shown in FIG. 11$a$-$c$ (Patient 1) and FIG. 11$d$-$f$ (Patient 2). Across the group, classification performance was significantly higher than chance (0.54 vs 0.50, 431)=5.2, P<0.0001 permutation test, FIG. 11$g$), which was critical to establish the feasibility of using the classifier to decode encoding efficiency. Classifier weights were largest in hippocampus, occipital cortex, MTL and prefrontal cortex (FIG. 11$h$), areas targeted in later stimulation sessions. Classification was also performed using the distribution of spectral power across electrodes within individual time-frequency bins (FIG. 11$i$), which suggested classifier performance was highest in high-frequency, low 0 (1-3 Hz) and high 0 (4-8 Hz) ranges beginning at 500 ms post-word onset.

The classifier output for a given input observation reflects the model's confidence in its classification decision, i.e. that the observation belongs to the recalled vs. forgotten category. If this is true, subjects should be more likely to recall a word if the classifier is highly confident it will be recalled than if it is less confident. To test this, actual subject memory performance was calculated as a function of the classifier's output for each trial. The cross-validation procedure entailed testing the classifier on all encoded words, yielding an encoding efficiency estimate for each word. The estimates from all words from all sessions for that subject form a distribution over levels of classifier estimates of encoding efficiency. This distribution was sorted into terciles and then subjects' recall performance varied across bins was evaluated. For each tercile, recall performance was computed for words in the tercile, the subject's overall mean recall performance was subtracted and this difference was divided by the overall mean (Supplemental Methods). This is a normalized measure that estimates the classifier's effectiveness in assigning recalled words to the highest tercile and forgotten words to the lowest tercile. (FIG. 11$c$,$f$). Mean recall performance was significantly higher for words in the high tercile of classifier output compared to the low tercile (High: 18.7±4.9%, Low: −18.5±4.1%; t(31)=4.4, P<0.0002; FIG. 11$j$). This suggested that classifier output could be used as a continuous estimate of encoding efficiency suggesting the classifier could be used to predict stimulation's effect on memory.

In the stimulation sessions, bipolar stimulation was applied to a single pair of electrodes in alternating blocks during the encoding phase of each list. Each block lasted for a pair of words so that each list of 12 words included three pairs of stimulated words and three pairs of unstimulated words. The experimental design for the stimulation sessions also included several word lists during which no stimulation was applied (NoStim lists), which was important as a baseline for behavioral performance, and for testing the generalization of the classifier trained on the previous record-only sessions.

Classifier AUC for NoStim lists was significantly greater than chance (0.53 vs. 0.50, P=0.05, permutation test), showing that patterns of brain activity associated with successful memory during the record-only sessions predicted memory performance in the independent stimulation sessions. Memory performance for NoStim lists was similar to performance during the previous record-only sessions (mean recall 26.8±1.9%, P>0.20). Memory performance on NoStim lists was used as a baseline for assessing the overall behavioral effects of stimulation. Recall did not significantly differ for stimulated words relative to the NoStim baseline (25.4±1.7%; P>0.25). There was also no evidence that stimulation interfered with recall of non-stimulated words on the same list (26.7±2.1%; P>0.23). Stimulation did not affect the serial position curve nor the lag-conditional response probability curve, two traditional assays of performance in the study of human memory (FIG. 12a). These findings demonstrated little to no effect of stimulation on memory performance across the group.

Although stimulation did not have consistent memory effects across the group, individual subject data suggested stimulation sometimes had quite strong effects (FIG. 12b). This might be because stimulation strongly modulated neural activity in some subjects and had no effect in others. To test this, each subject's classifier was used to estimate encoding efficiency for words encoded immediately after stimulation offset. Average encoding efficiency was also computed for matched epochs in the NoStim lists and this baseline was subtracted from the stimulation condition. For subjects with elevated encoding efficiency post-stimulation, recall performance was likely to be increased while the reverse was true for subjects with decreased encoding efficiency (425)=0.33, FIG. 12c solid line). A permutation procedure was used to confirm that this effect was not driven by variability in classifier output across subjects, which should correlate with memory performance if the classifier shows above chance performance (FIG. 12c dashed line, P<0.02).

To understand how stimulation might enhance or depress memory function, some embodiments consider whether stimulation might be more likely to positively affect memory encoding if it is delivered when the brain is in a low-efficiency encoding state. To test this idea the classifier was used to estimate encoding efficiency for the intervals just prior to stimulation delivery (FIG. 10c) and the distribution was sorted again across trials into high and low terciles. Subjects' memory performance was then analyzed for words following stimulation offset (i.e. two list positions later), conditioned on the classifier's estimate of the encoding state just prior to stimulation (FIG. 13). Stimulation condition significantly interacted with encoding state (F(1, 28)=4.58, P<0.05) such memory was higher than the NoStim condition if stimulation arrived when encoding efficiency was poor (t(28)=1.92, P=0.06), but was lower if stimulation arrived when encoding efficiency was high. The slope of the behavioral effect of stimulation was also negative across terciles (−12.4±9.5%) and was marginally different from the positive slope observed for the non-stimulated condition (18.8±10.1%, t(28)=2.01, P=0.054).

The data showed that neural activity collected during encoding is predictive of later memory performance. The data showed that multivariate patterns of neural activity that reflect encoding efficiency can be modulated using targeted electrical stimulation. The extent to which stimulation affected activity in the encoding network was predictive of the extent to which stimulation affected memory performance. The data showed that changes in memory performance were correlated with stimulation-induced changes brain physiology, and linked stimulation's effects to the brain state at the time it was applied. This demonstrates that direct perturbation of encoding activity leads to predictable changes in memory performance.

It was shown that multivariate statistical decoding of neural activity can be used to infer brain states that are associated with successful memory encoding, and that such decoding can also be applied to predict the behavioral effects of electrical stimulation. Although the decoding of neural activity was conducted in an offline post-processing stage, a natural extension of this work would be to implement multivariate decoding in a closed-loop system to guide stimulation in real-time. Closed-loop approaches have been applied to the training of attention using fMRI and to maximizing the benefit of restudy events using scalp EEG. By showing that iEEG stimulation is most likely to improve memory when neural encoding efficiency is low just prior to stimulation delivery, the work provides the foundation for future closed-loop approaches to apply stimulation when it is likely to be most effective in improving memory encoding. Future therapies may be able to exploit neural decoding in real-time to optimally stimulation to treat the symptoms of memory disorders.

Methods Participants.

Patients undergoing intracranial electroencephalographic monitoring as part of clinical treatment for pharmacologically-resistant epilepsy were recruited to participate in this study. Data were collected as part of a multi-center study designed to assess the effects of electrical stimulation on memory-related brain function. Data were collected at the following centers: Thomas Jefferson University Hospital (Philadelphia, Pa.), Hospital of the University of Pennsylvania (Philadelphia, Pa.), Mayo Clinic (Rochester, Minn.), Dartmouth Medical Center (Hanover, N.H.), Emory Hospital (Atlanta, Ga.) and University of Texas Southwestern Medical Center (Dallas, Tex.). The research protocol was approved by the IRB at each hospital and informed consent was obtained from the participants and their guardians.

Electrophysiological data were collected from electrodes implanted subdurally on the cortical surface as well as deep within the brain parenchyma. In each case, the clinical team determined the placement of the electrodes so as to best localize epileptogenic regions. Subdural contacts were arranged in both strip and grid configurations with an inter-contact spacing of 10 mm for surface contacts and 5 mm for depth contacts.

Anatomical Localization.

Anatomical localization of electrode placement was accomplished using a two step process. First, hippocampal subfields and MTL cortices were automatically labeled in a pre-implant T2-weighted MM using the automatic segmentation of hippocampal subfields (ASHS) multi-atlas segmentation method. This dedicated T2-weighted sequence provides tissue contrast at anatomical boundaries between hippocampal subfields and MTL cortical subregions, enabling automatic delineation of these areas. Following this automatic labeling procedure, a post-implant CT scan was co-registered with the MRI using Advanced Normalization Tools. Electrodes that are visible in the CT were then localized within the MTL subregions by a pair of expert neuroradiologists, specializing in MTL anatomy. The neuroradiologists confirmed the output of the automated pipeline, and provided additional detail on localization within subfield/subregions.

Electrophysiological Recordings and Data Processing.

Intracranial data were recorded using one of the following clinical electroencephalogram (EEG) systems (depending the site of data collection): Nihon Kohden EEG-1200, Natus XLTek EMU 128 or Grass Aura-LTM64. Depending on the amplifier and the preference of the clinical team, the signals were sampled at either 500 or 1000 Hz and were referenced to a common contact placed either intracranially, on the scalp or mastoid process. A 5 Hz band-stop first order Butterworth filter around 60 Hz was applied to remove signal from electrical line noise. A bipolar referencing montage was then generated for each subject by taking the difference between the voltage timeseries recorded at all pairs of spatially adjacent electrodes. A spectral decomposition on the voltage timeseries was computed for each bipolar-referenced signal. For the record-only sessions, wavelet decomposition was used to extract power across a set of 50 logarithmically-spaced frequencies between 1 and 200 Hz (wave number=7). Wavelet decomposition was computed for each 1600 ms word encoding epoch, with an additional 1500 ms buffer period before and after that was discarded to remove convolution edge effects. The resulting time-frequency data were then averaged into larger 100 ms time bins, with 100 ms spacing.

Verbal Memory Task.

Each subject participated in a delayed free-recall task in which they were instructed to study lists of words for a later memory test; no encoding task was used. Lists were composed of 12 words chosen at random and without replacement from a pool of high frequency nouns (either English or Spanish, depending on the participant's native language; http://memory.psych.upenn.edu/WordPools). Each word remained on the screen for 1600 ms, followed by a randomly jittered 750-1000 ms blank inter-stimulus interval (ISI).

Immediately following the final word in each list, participants performed a distractor task (20 seconds) consisting of a series of arithmetic problems of the form A+B+C=??, where A, B and C were randomly chosen integers ranging from 1-9. Following the distractor task participants were given 30 seconds to verbally recall as many words as possible from the list in any order; vocal responses were digitally recorded and later manually scored for analysis. Each session consisted of 25 lists of this encoding-distractor-recall procedure. Each participant performed at least two sessions of the passive recording version of the verbal memory task, and two sessions of the stimulation version of the task.

Stimulation Methods.

For each stimulation session, electrical current was passed through a single pair of adjacent electrode contacts. At the start of each session, a safe amplitude was determined for stimulation using a mapping procedure in which stimulation was applied at 0.5 mA while a neurologist monitored for after discharges.

In some embodiments, this procedure was repeated, incrementing the amplitude in steps of 0.5 mA, up to a maximum of 1.5 mA for depth contacts and 3.5 mA for cortical surface contacts. These maximum amplitudes were chosen to be well below accepted safety limits for charge density. Stimulation was delivered using charge-balanced biphasic rectangular pulses (pulse width=300 µs) at 50 Hz frequency. During the encoding phase, stimulation was applied continuously for 4.6 s while subjects encoded two consecutive words; stimulation was not applied for the following two; and this alternation procedure continued until the end of the list. Each 4.6 s block of stimulation began 200 ms prior to the presentation of a word on the screen and lasted until 200-450 ms after the offset of the next word. Stimulation was applied in 20 of the 25 lists in a session, and each stimulation list was randomly chosen to begin with a stimulated or non-stimulated pair of words. The order of the 20 stimulation lists and 5 non-stimulation lists was randomized within each session. The non-stimulation lists served as a baseline for the analysis of behavioral data and intracranial recordings.

Machine Learning Classification.

Spectral power averaged across the time dimension was used for each word encoding epoch as the input to a logistic regression classifier. Thus, the features for each individual word encoding observation were the average power across time, at each of the 50 frequencies at each electrode. L2-penalization and a cross-validation approach was used to select the optimal penalty parameter before applying this parameter during our final cross-validated model training. To select the penalty parameter, a set of 25 logarithmically-spaced penalty parameters was generated from 100 to 5000. For each possible penalty parameter, five-fold leave-one out cross-validation was computed to generate a classifier probability estimate for each word encoding observation. A receiver operating characteristic (ROC) curve was then computed for the set of classifier estimates derived from testing each penalty parameter in each crossvalidation fold. The penalty parameter that yielded the largest mean AUC over cross-validation folds was chosen for use in final model training and testing.

For the stimulation sessions, the spectral decomposition was computed for the −900 to −100 ms period prior to onset of each stimulation event using the multitaper method. The bipolar referenced voltage signal was projected onto a set of three orthogonal Slepian windows (2 Hz bandwidth) before decomposition with the Fast Fourier Transform. Zero-padding of the signal was used to achieve the desired frequency resolution. A window size of 400 ms was used and the multitaper estimate was computed at each sample in the 800 ms period of interest. Power within desired frequencies was averaged across all estimates from the 800 ms pre-stimulation period, for all electrodes in the subject's montage. This set of features (50 frequencies×N electrodes) was then used as a set of observations and input to a logistic regression classifier that had been trained on data from the record-only period. This produced a model-derived estimate of the probability that the brain was in an efficient encoding state just prior to stimulation onset. The preceding analysis for the 100 to 2100 ms period was conducted following stimulation offset. Electrical artifacts precluded analysis of the stimulation interval itself.

Behavioral Analysis.

The percentage of words recalled from the encoding lists was used as a behavioral measure of memory performance. Within the experimental design, memory performance was determined in four conditions: record-only words, stimulated words, non-stimulated words encoded in the same list as stimulated words, and non-stimulated words encoded in non-stimulated lists (NoStim). The overall effects of stimulation on memory was analyzed by comparing recall performance for Stim words to NoStim words using two standard measures, the serial position curve (SPC; FIG. 12a, top) and the lag conditional response probability curve (CRP; FIG. 12a, bottom). The SPC depicts the probability of recalling a studied word as a function of its position within the study list. The CRP depicts the probability of recalling two words from the study list as a function of the lag (in number of words) between the serial positions of the two words.

Analysis Stimulation's Effect on Memory Performance.

Because electrical artifacts evoked by our stimulation trains precluded direct analysis of the stimulation epochs themselves, the analysis of the relationship between stimulation and memory performance focused on epochs prior and following the stimulation trains. To quantify the effect of stimulation on encoding efficiency during these periods, estimates of encoding efficiency were computed using a multivariate model for pre-stimulation and post-stimulation periods. An inverse logic transform was used to convert the classifier estimates on these measures. The same analysis was conducted for matched epochs within NoStim lists, which served as our baseline measure of encoding efficiency for each patient. A percent change measure $$\Delta EE = 100 * \frac{EE_{Stim} - EE_{NoStim}}{EE_{NoStim}},$$

was computed where $EE_X$ is the mean encoding efficiency across trials in condition X. This measure accounts for differences in subjects' baseline levels of recall performance.

A similar measure was computed to quantify the stimulation-related change in recall relative to NoStim baseline for words encoded immediately following stimulation offset:

$$\Delta RR = 100 * \frac{RR_{Post-Stim} - RR_{Post-NoStim}}{RR_{Post-NoStim}},$$

where $RR_X$ refers to the recall rate in condition X. We computed the across-subject correlation between ΔEE and ΔRR (FIG. 12c) and assessed significance using a bootstrapping procedure. Within each of 1000 permutations, the Stim/NoStim labels were randomly shuffled at the word-level within-subject. ΔEE and ΔRR was computed on the permuted data for each subject before computing the across-subject correlation between these measures on the permuted data. A p-value was derived by comparing the true Pearson's r with the distribution of r-values generated by the permutation procedure.

To assess the effects of stimulation on recall rate as a function of the degree of encoding efficiency just prior to stimulation delivery, a normalized measure of memory was used for the post-stimulation words, ΔRR, but split trials into terciles based on each subject's distribution of prestimulation EE values. ΔRR was analyzed as a function of tercile (lowest/highest) and stimulation condition (Stim/NoStim) using a 2×2 analysis of variance (FIG. 13).

Attached herewith is an Appendix that illustrates one or more embodiments of the present inventions described herein.

In at least one embodiment, there is included one or more computers having one or more processors and memory (e.g., one or more nonvolatile storage devices). In some embodiments, memory or computer readable storage medium of memory stores programs, modules and data structures, or a subset thereof for a processor to control and run the various systems and methods disclosed herein. In one embodiment, a non-transitory computer readable storage medium having stored thereon computer-executable instructions which, when executed by a processor, perform one or more of the methods disclosed herein.

It will be appreciated by those skilled in the art that changes could be made to the exemplary embodiments shown and described herein without departing from the broad inventive concept thereof. It is understood, therefore, that this invention is not limited to the exemplary embodiments shown and described, but it is intended to cover modifications within the spirit and scope of the present invention as defined by the claims. For example, specific features of the exemplary embodiments may or may not be part of the claimed invention and features of the disclosed embodiments may be combined. Unless specifically set forth herein, the terms "a", "an" and "the" are not limited to one element but instead should be read as meaning "at least one".

It is to be understood that at least some of the figures and descriptions of the invention have been simplified to focus on elements that are relevant for a clear understanding of the invention, while eliminating, for purposes of clarity, other elements that those of ordinary skill in the art will appreciate may also comprise a portion of the invention. However, because such elements are well known in the art, and because they do not necessarily facilitate a better understanding of the invention, a description of such elements is not provided herein.

Further, to the extent that the method does not rely on the particular order of steps set forth herein, the particular order of the steps should not be construed as limitation on the claims. The claims directed to the method of the present invention should not be limited to the performance of their steps in the order written, and one skilled in the art can readily appreciate that the steps may be varied and still remain within the spirit and scope of the present invention.

What is claimed is:

1. A method for delivering stimulation to alter a cognitive state of a user, the method comprising:
   during a testing phase:
      presenting a plurality of test items to the user;
      receiving a plurality of responses and a plurality of testing phase brain signals from the user;
      associating each of the plurality of responses and each of the plurality of the testing phase brain signals with each of the plurality of test items;
      determining that each of the testing phase brain signals corresponds to one of: a high-performance cognitive state of the user and a low-performance cognitive state of the user, using the associated test item and associated response; and
      in response to determining that each of the testing phase brain signals corresponds to one of: a high-performance cognitive state of the user and a low-performance cognitive state of the user, generating a testing phase biomarker using the plurality of testing phase brain signals that corresponds to the one of: the high-performance cognitive state of the user and low-performance cognitive state of the user, wherein the testing phase biomarker is a representation of electrophysiological data;
   during a stimulation phase occurring after the testing phase:
      monitoring a stimulation phase brain signal from the user;
      evaluating the cognitive state of the user by comparing the stimulation phase brain signal of the user with the testing phase biomarker;
   delivering stimulation to a brain of the user based on the evaluating step to steer the brain of the user towards one of: the high-performance cognitive state of the user and the low-performance cognitive state of the user.

2. The method of claim 1, wherein the testing phase biomarker is a set of one or more features that distinguish a respective brain signal that corresponds to the high performance cognitive state from a respective brain signal that corresponds to the low performance cognitive state of the user.

3. The method of claim 1, wherein the testing phase biomarker is associated with a threshold corresponding to a feature of a respective brain signal.

4. The method of claim 1, further comprising: transmitting the testing phase biomarker to a modulation device.

5. The method of claim 1, further comprising: receiving the testing phase brain signals from a modulation device connected to the brain of the user.

6. The method of claim 1, further comprising: associating the plurality of responses with the plurality of test items by comparing the plurality of responses to the plurality of test items.

7. The method of claim 1, further comprising: associating the testing phase brain signal with the plurality of test items by determining whether a time period where the testing phase brain signals are monitored by a modulation device overlaps with a time period where the plurality of test items is presented to the user.

8. The method of claim 1, wherein if the response matches the plurality of test items, the response is a positive response.

9. The method of claim 1, wherein the testing phase brain signal corresponds to the high-performance cognitive state of the user if the testing phase brain signals are associated with plurality of test items having a positive response.

10. The method of claim 1, wherein if a respective response does not match the plurality of test items, the respective response is a negative response.

11. The method of claim 1, wherein the testing phase brain signals corresponds to the low performance cognitive state of the user if the brain signals are associated with a plurality of test items having a negative response.

12. The method of claim 1, wherein the high performance cognitive state is an accurate memory.

13. The method of claim 1, wherein the low performance cognitive state is an inaccurate memory.

14. The method of claim 1, further comprising:
storing the testing phase biomarker in a database.

15. The method of claim 1, wherein the testing phase brain signals are one or more brain signals from one or more users.

16. The method of claim 1, further comprising:
generating a biomarker representative value by applying a dimensionality reduction algorithm to one of: the testing phase biomarker and the testing phase brain signals.

17. The method of claim 1, further comprising:
optimizing stimulation parameters by applying stimulation to the user using a plurality of selected parameters and selecting one or more of the plurality of selected parameters that causes a desired effect on the user.

18. A system for creating a biomarker indicative of high performance or low performance cognitive state according to the method of claim 1.

19. A non-transitory computer readable storage medium having stored thereon computer executable instructions which, when executed by a processor, perform any of the methods for creating a biomarker indicative of high performance or low performance cognitive state according to the method of claim 1.

20. The method of claim 1, wherein the testing phase biomarker is indicative of the low performance cognitive state of the user as determined based on a cognitive test performed on a contributor.

21. The method of claim 1, wherein the testing phase biomarker is indicative of a high performance cognitive state of the user as determined based on a cognitive test performed on a contributor.

22. The method of claim 20, wherein the contributor is the user.

23. The method of claim 20, wherein the contributor is a plurality of contributors.

24. The method of claim 20, wherein the contributor is different than the user.

25. The method of claim 1, further comprising:
updating the testing phase biomarker based on the testing phase brain signal of the user and a response of the user to the plurality of test items.

26. The method of claim 1, wherein electrical stimulation is delivered to a single subfield of a hippocampus.

27. The method of claim 1, wherein electrical stimulation is delivered to multiple regions of the brain of the user.

28. The method of claim 1, wherein comparing the stimulation phase brain signal to the testing phase biomarker includes comparing the stimulation phase brain signal to a biomarker representative value generated by applying a dimensionality reduction algorithm to the testing phase biomarker.

29. The method of claim 1, wherein stimulation delivered to the brain of the user is based on predetermined stimulation optimization parameters derived before the monitoring step and configured to steer the brain of the user towards high performance cognitive state.

* * * * *

UNITED STATES PATENT AND TRADEMARK OFFICE
CERTIFICATE OF CORRECTION

| | | |
|---|---|---|
| PATENT NO. | : 10,449,359 B2 | |
| APPLICATION NO. | : 15/545927 | |
| DATED | : October 22, 2019 | |
| INVENTOR(S) | : Michael Kahana and Daniel S. Rizzuto | |

It is certified that error appears in the above-identified patent and that said Letters Patent is hereby corrected as shown below:

In the Specification

On Column 1, Lines 21-24, after "GOVERNMENT SUPPORT":
"The present invention was made with Government support under Grant No . N66001-14-2-4032 awarded by Space and Naval Warfare Systems Center , Pacific. The Government has certain rights in the invention."

Should read:
--This invention was made with government support under grant numbers MH055687, MH069175 awarded by the National Institutes of Health. The government has certain rights in the invention.--

Signed and Sealed this
Thirty-first Day of May, 2022

Katherine Kelly Vidal
*Director of the United States Patent and Trademark Office*